(12) United States Patent
Wang et al.

(10) Patent No.: US 7,056,743 B2
(45) Date of Patent: Jun. 6, 2006

(54) MTHP PROMOTER ELEMENT

(75) Inventors: Zengyu Wang, Ardmore, OK (US); Maria Harrison, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 54 days.

(21) Appl. No.: 10/817,767

(22) Filed: Apr. 2, 2004

(65) Prior Publication Data

US 2005/0003479 A1 Jan. 6, 2005

Related U.S. Application Data

(60) Provisional application No. 60/459,903, filed on Apr. 2, 2003.

(51) Int. Cl.
*C12N 15/82* (2006.01)
*C12N 5/14* (2006.01)
*C12N 15/90* (2006.01)
*A01H 5/00* (2006.01)
*A01H 5/10* (2006.01)

(52) U.S. Cl. ................ 435/468; 435/320.1; 435/419; 536/24.1; 800/278

(58) Field of Classification Search ........... 800/278, 800/295, 298; 435/320.1, 419, 468; 536/23.1, 536/23.6, 29.1, 24.1
See application file for complete search history.

(56) References Cited

U.S. PATENT DOCUMENTS 5,641,876 A 6/1997 McElroy et al. ........... 536/24.1

OTHER PUBLICATIONS

Kim et al. 1994. Plant Mol Biol. vol. 24, pp. 105-117.*
Cashmore, "Nuclear genes encoding the small amount subunit of ribulose-1,5- biphosphate carboxylase," *Gen. Eng. of Plants*, Plenum Press, NY, 29-38, 1983.
Lindstrom et al., "Expression of soybean lectin gene deletions in Tobacco," *Developmental Genetics*, 11:160-167, 1990.
Mylona et al., "The root epidermis-specific pea gene RH2 is homologous to a pathogenesis-related gene," *Plant Mol. Biol.*, 26:39-50, 1994.
Odell et al., "Identification of DNA sequences required for activity of the cauliflower mosaic virus 35S promoter," *Nature*, 313:810-812, 1985.
Paszowski et al., "Direct gene transfer to plants," *EMBO J.*, 3(12):2719-2722, 1984.
Poulsen et al., "Characterization of an rbcS gene from *Nicotiana plumbaginifolia* and expression of an rbcS-CAT chimeric gene in homologous and heterologous nuclear background," *Mol. Gen. Genet.*, 205(2):193-200, 1986.
Vodkin et al., "cA lectin gene insertion has the structural features of a transposable element," *Cell*, 34:1023-1031, 1983.
Wang et al., "Characterization of cis-acting elements regulating transcription from the promoter of a constitutively active rice actin gene," *Mol. Cell Biol.*, 12(8):3399-3406, 1992.
Database Accession No. AJ503174, Jul. 31, 2002.

* cited by examiner

*Primary Examiner*—Ashwin Mehta
(74) *Attorney, Agent, or Firm*—Fulbright & Jaworski L.L.P.

(57) ABSTRACT

The invention provides MtHP promoter sequences capable of functioning as a strong plant promoter. Compositions comprising these sequences described, as are transgenic cells transformed with such sequences. Further provided by the invention are methods for the expression of transgenes in plant and other cells comprising the use of these sequences. The sequences of the invention represent a valuable new tool for the creation of transgenic cells expressing one or more selected coding regions.

33 Claims, 15 Drawing Sheets

TTCATTATTCTTCTTACACTAGCATTATAATTCATCATGGGTGTCATCATCAATTTGAGGAAGAAACCACCTCTGTTGTA
GCTCCAGCTACACTTCACAAAGCTTTTGTTACAGATGCTGACAACCTTATCCCAAAGTTATTGATGTCATCAAAAGTAT
TGACATTGTTGAAGGAAATGGTGGCGCCGGAACCATCAAGAAACTCACTTTCGTTGAAGATGGTGAAACCAAGTATGATT
TACACAAAGTGGAGTTAGTAGATGCTAACTGGCTTACAACTACAGCATTGTTGGAGGTGATAGTCTTCCAGACACA
GTAGAGAAGATTTCATTTGAAGCTAAACTGTCTGCAGGTCCAAATGGAGGATCCATTGCAAAACTTAGTGTGAAATACTT
TACAAAAGGAGATGTTACTCCAAGTGAAGAGAACTCAAGAGTGGCAAAGCTAAGGTGATGGTCTTTTCAAGGCCCTTG
AGGGTTACTGTTGGCTAATCCTGATTACAACTAAAGCATATAATTCTCTATTTTCCCCCTTTCCTTTTGGTAAGGAAGTTTGA
AAGCTATATCCAGTTGCTTAATTGGGTACCAATGTAATTCTCTATTTTCCCCCTTTCCTTTTGGTAAGGAAGTTTGA
GTGTGAGATTGTAAGTCATGAGTGCCCTCCCCTTCAAAACATTGTCAGCTTTTTTTAATAAAGAGATTGTTACTATTT

FIG. 1

```
CTCGATCAATAGTTCAAACCAAGAAGAAATTCAAGAATTAGCCAAAGCCCAAACACATATAGGGATTAAGCCACCAATTATGATAAAA
AAAAAAGAGACTTTTTGCATTCAGTCATCGATAGAAAATGAGCTTAATGTTATCTAAAAATTGAAGAGCTGAGCTTGTTGTATTATTAAATATC
TTGTCGTTTCTTTCTTCTGTATAACCTACGTGCAAGCAAACCAAATCATCAACATAAACACTTGTTAATGAGCGGCGGATTTGAAACACCTTCTAAACACTTTT
TTTCTAAATAAAACTTAATGAATGTTTCCTTTTTGAACTCTTAACAAACACTTAGAACACTTGTTAATAGTAAACACTGTTAAAAAATGAAGAAATATAATTGTA
TTTATTAAAATTACTAAAAATATGTAAAATTGATTTGAAATGTTCCGATGCTTATTGAAATTGATTTTTATCTCTATAATTATATAACTTGGCTCT
AGAACTTAGAAACCATTTTAATTTTTAATGATTTTATATCCAAAAATTGTTGGCAAAACTAAACCGCGACACGCGGACATGAACCAAGTTGTTTGGCCTCCGTGG
TCACATTTAACCATTTTAACTAATCATTTTATTTGAAAAAATCATTTCACAGAGGAACAAACGCTTGACCCAATTGCATGAGCCAGATTAGTCACCAA
AAAGGAGCTCTTTCCAAGATGTATCCGGAAAATACCGGACTCGATTCACAGAGGAACAAACGCTTGACCCAATTGCATGAGCCAGATTAGTCACCAA
CCTTTGTGGGGTCGAAAACTGGTGCAAAACAAATAGTATTATTGTCCGGATTCTAGAATGGCGTTCTGAATTGATCGTGTAAAAGAAATCTAGATACAAGATACGCAGA
AAAAAAACAAAATCTATATTGTAAAACAAATAGTACCTGCAACATAATTTCCTCTCTTTTTGGGTTTGCATTGAAATTTGAAATTGAAATTGAAAGATATAAGAGCAAGAAAAAAA
TAAATAAAAATGAGAGACTGCCATAGCTTTTGTGAACCCAAATAATTTTCTTATTTGAATAGTATATCAGGAATTTGAAATTGCATATCAAGATGTTCAACAACTGATATTAG
TTAGTCATCATCTTTATCTAATTAGCAATCTAAAGTCCAAACAATACTGTACCAAAAAAAGTCTAAATAACAATTTAAATCAACTTCAGTTCCTATAAATACTAGC
CATAACTACATTCATAAACCACATTACGACCATTATTGTTATTTCTTACCTAGCATTTAATACATTATACCATCatggtgtttcaatttga
ggatgaaccacctctaatgtagctcctgctacacttacaaagctcctagttacagattctgataacctatccaaaggttattgatgtcatcaaga
gtgttgaaattgtgaaggcaacggtggcgccgaaccatcaagaaacttactttttgttgaaGGTCGGTATAAATATATATTATTTTACTTTATTGTC
AATATTAATAATTAGTTGTTACGTTGTTTAAAAAAATATGTTTTCGACATCGAGTCTAAGTTCAGTAGCTCAGTATGATGAACTATACCTAGTAATGCTGATGA
TGTTTGTGATTGTGAAACGGATCAATATGCAGATGGTGAGACCACTGAGAATCAATAATCAGACAGAAGAATCAATATCAGATATTTTACAGACTCTCTTTTTACCAATT
ACACATCTGTCATATGAACATCAAATGTGGTTTGCCAAAAATGTGCGAACTCGATATTTTACAGACTCTCTTTACCGAACTGGCCGTA
CTGCCCGAATTACACTTGAAACGATCTCAACAGTTAACGTTGGCTTGCCTGCCACGCTTGCCTTGCTGCTGAAACTCTCACTCTTACCGAACTGGCCGTA
ACCTGCCAACCAAGCGAGAACAGAAACATAACATCAAACGAATCAAACATCAAACCAAGCCCATCGATTGTTGACTGGTCTGATATCCGTGAGCAAAAACGGCTTATGGTATTGCGAGC
TGGCATGCGCTAGCTTTATCGTGTCGGGCAATACATGCCCATTGTAACTCTTATGAGAAAGCGTTCCCGCTTCAGAGCAATGTTCAAAGAAAAGCTCATGACCAATTTCTAGCCG
ACTTGGCGAGCATTCTACCGAGTAACACCACACCGTCACTAAGAGGCTGACTAAGAAAGTACAATATGCAGACCTAGGACGGAAAACTATCGCAAATGCCATGGTTCTCAGCCTCATCATCAGTCA
TACTGGTTAAGTCGAGTAAGAGAAGAAAGGCTGACTAAGAGGCTGACTAAGAGGCTGACTAAGCCATGAAATCTATTGTTATAAATGAACTTCGCTCTAAAGGCCGAAAAATCAGC
GCTCAAAGACTTAGGCTATAAGAGGCTCACCACCCGTCACTAAAAGCAATCATGCCAAAATCTACTCAGATTGAAAGTCCTGCTTGCCTAAGAGTCCTGCCTACGGACTAGGCCTACG
CGAACACCCAAAACAACGGACCAGCTCAGAGCTTCCAGGCTCATCATGTAGGGCATGAAGTTCGGATGAAGCTCAATCGAAAGCTACATGGGGCATAAACATGTTGCGCATGCTCAGA
AACAAGGTTGGGACAAGCAGCACTTCCAGGTCACACACTTCGTCGGCTCGTAACAATCGAAATCGAGAAATCGAAACCCTCCAACACCTTACGCTTAGGCATGAAGTTCGGGAATTATGAGGGATCT
TACACAATAACAAGGAAGAAGACTTACTCGTCGGCTCGTAACAATCGAAATCGAGAAATCGAGAAATCGAAACCCTACTACTACAACCTGCGTTAGGCATGAAGTTCGGGAATTATGAGGGATCT
CTCAGaccaagcatgtgtacacaaagtggagttagtagtgatgatggcttacaacagcattgttggagtgttggccttccagacac
aatagagaagattcatttgaggctaaattgtctgcaggtccaaatggaggatccaCTAGTTCTAGAGCGGCCGCCACCGCGGTGGAGCTCCAATTC
GCCCTATAGTGAGTCGTATTACGCGCGCTCACTGGCCGTAATAGCGAAGAGGCCCGCACCGATCGCCCTTCCCAACAGTTGCGCAGCCTGAATGGCGAATGGCGCCC
CACATCCCCTTTCGCCAGCTGGCGTAATAGCGAAGAGGCCCGCACCGATCGCCCTTCCCAACAGTTGCGCAGCCTGAATGGCGAATGGCGCCC
TGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTT
TCTCGCCACGTTCGCCGGCTTT
```

FIG. 5

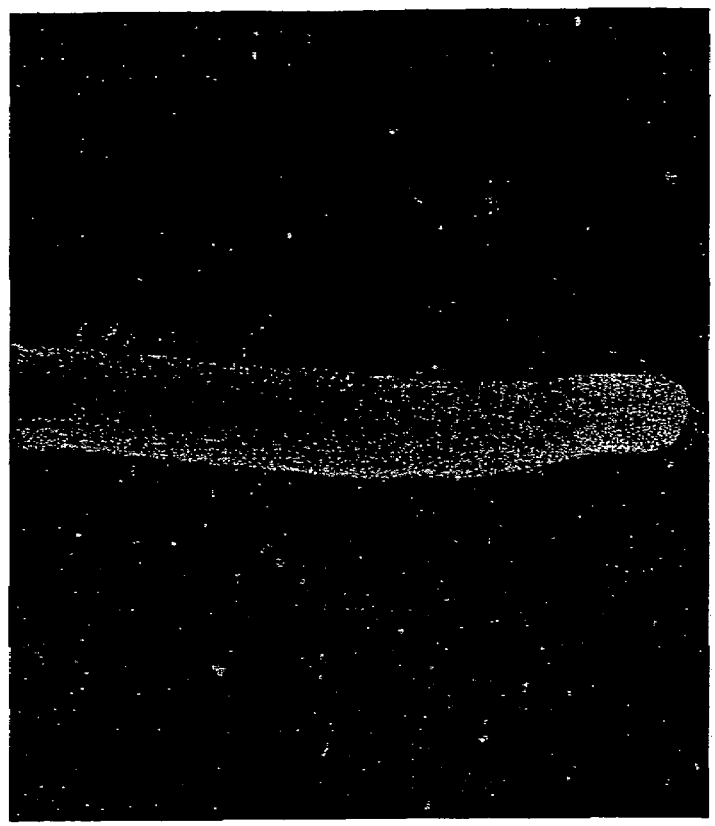
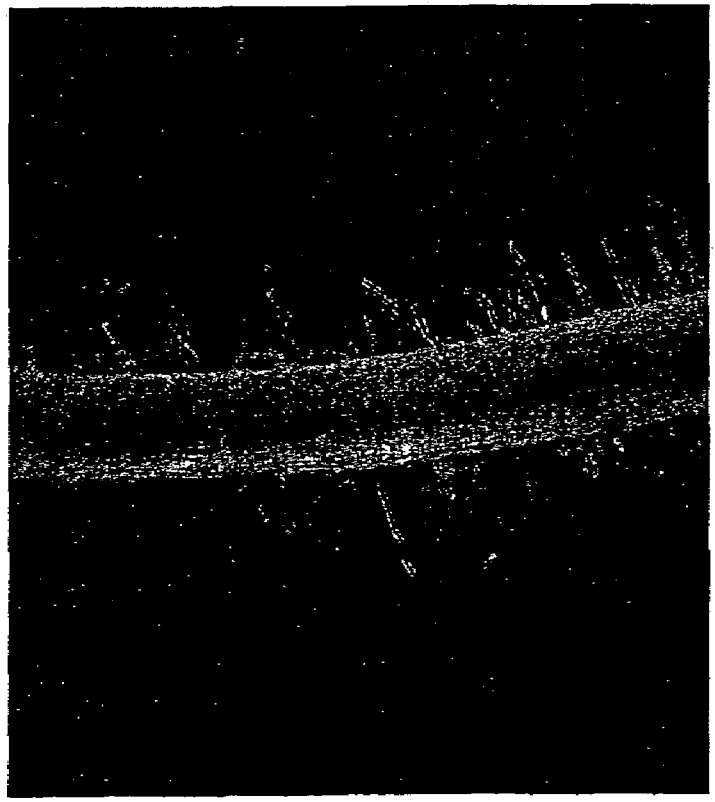
FIG. 7

```
     CTCGATCAAT AGTTCAAACC AAGAAAACA AAAATGAATT CAAGAATTAG CCAAAGCCCA AACACATATA GGGATTAAGC
     CACCAATTAT GATAAAAAA AAAAAGAAG ACTTTTTGC ATTCAGTCAT CGATAGAAAA TGAGCTTAAT GTTATCTAAA
     AATTGAAGAG CTGAGCTTGT TGTATTATTA AATATCTTGT CGTTTCTTTC TCTAAACACCT TTTCTGTATA ACCTACGTGC AAGCAAACCA
     AATCATCAAC ATAAATGAGC GGCGGGATTT AAAAACACTT TCTAAACACCT TTAATAGTAA AAAATGAAGA ATATAAAACTT AATGAATGTT
     TCCTTTTTTG AATCTTTAAC AAAAACACTT AGAACACTTG TTAATAGTAA AAAATGAAGA ATATAAATTG TATTTTATTA
D5   AAATTTACTA AAAATAGTAT GATCCTCTTT TAGATTGAGT CCATATAAGA GTTTAAATAT AAAAATCATG
     GTTTGGCTCT CTCTATCGGG AAACCAAATA TGTAAAAATG ATTTGCCAT ATTTGTCCGA TGCTTATTGA AATTGATTTT
     TATCTCTATA ATTATATAAC TTGAAGTTAG AACTTAGAAC TGCAGCTTTT AATTTTTAAT ATGATTTTTA TACTCAAATT
D4   TAGCGTTCAA GGCACGCGGA CAAAACTAAA TTTAAATATA ACTAATTCAC ATTTAACCCA TTTTTAACTA AATCATTTA
     TTGAAAAAA AATTTGTTGG CAAAACTAAA CATGCACTAA ACCAAGTTGT TTGGCCTCCG GTGGAAAGGA GCTCTTTCCA
     AGAGATGTATC CGGAAAATAC TCACAGAGGG TCACAGAGGG GACCAATTG CATGAGCCAG ATTAGTCACC
     AACCTTTGGT GGGTCGAAAA CTGGTGCAAA AGCCAAAAAA TCCATTAAAA AACTAAACA CGCACTAAAT ATTTCCAACT
D3   AAAGTATTAG TATTATTTAA AAAAAAAACA AAAACTATAT ATAGTGCATG CAACATAATT TCCTCTCTT GGATTCTAGA
     ATGGGGTCTT GAGACTGAAT TGTTTAATAA TAAACAAATA TGAGAGACTG CAACATAATT TCCTCTCTT CCTAGCTTT
     TTTTGGGTTT GCATTTGATC GTGTAAAAGA GAAATCTAGA TACAAGAATA CGCAGATTTT GAATATATTG CCTAGCTTT
     TGTGGTTATT TGAATAGTAT ATCAGGAATT TTGAAATTTG ACTGGTCTTA GAGGAGATAA AAGAAGAAAA AAAAAATAGT
D2   ATATCAAGAA TTTTGTGAAC CCAAATAATT TTTTCTTTA AAATTCATAT CTCAATGTGA ATAATAAAAT GGTTCCAACA
D1   ACCTGATATT AGTTAGTCAT CATCTTTATC TAATTAGCAA TCTAAAGTCC AAACAATACT GTACCAAAAA AAGTCTAAAT
     AATACAACTT CAGTTCCTAT AATATCTAGG CATAACTACA TTCATAAACC ACACATTAGG ACCATTATTT GTTATTTCTT
Rev  ACCTAGCATT TTAATACATT ATACCATCAT G
```

FIG. 9

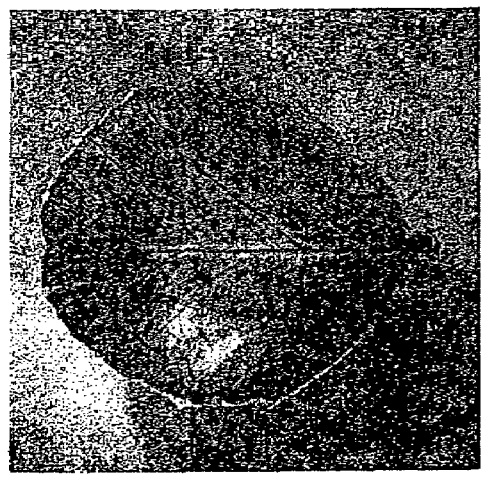
FIG. 13

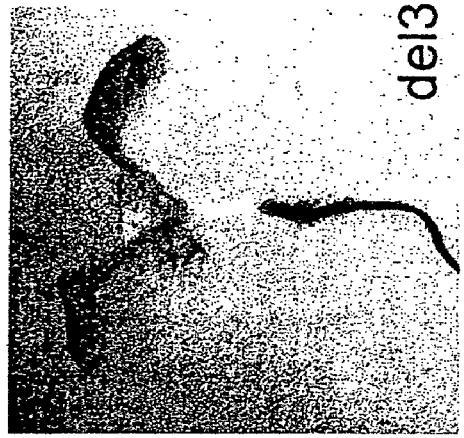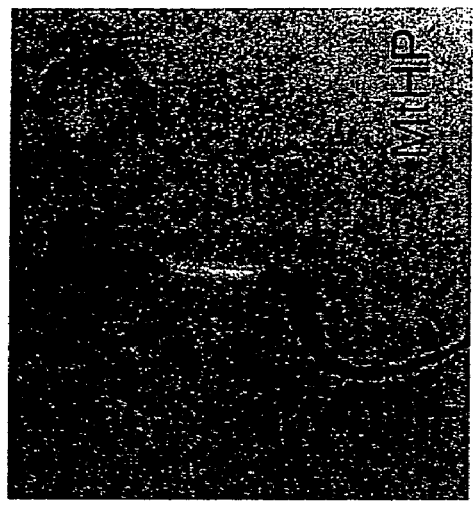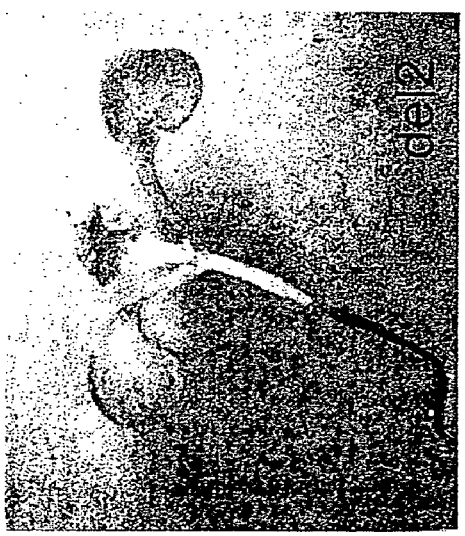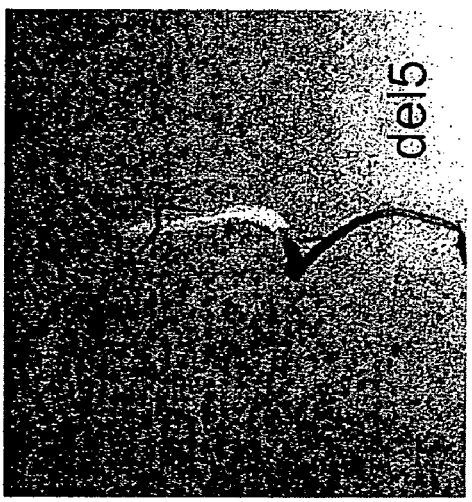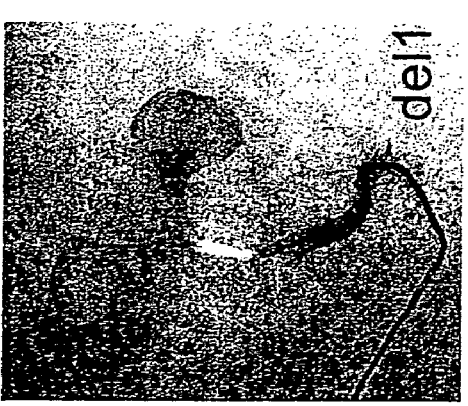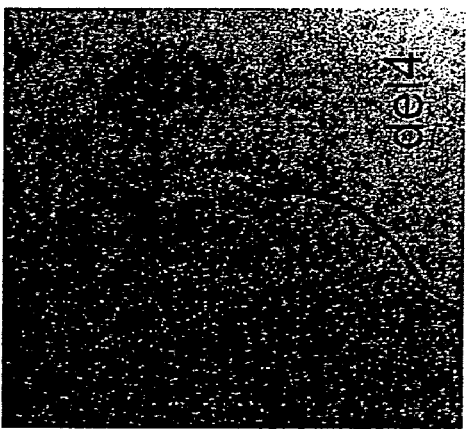
FIG. 14

SEQUENCE LISTING

<160> NUMBER OF SEQ ID NOS: 23

<210> SEQ ID NO 1
<211> LENGTH: 1551
<212> TYPE: DNA
<213> ORGANISM: Medicago truncatula

<400> SEQUENCE: 1

```
ctcgatcaat agttcaaacc aaagaaaaca aaatgaatt caagaattag ccaaagccca      60
aacacatata gggattaagc caccaattat gataaaaaaa aaaaagaag acttttttgc     120 attcagtcat cgatagaaaa tgagcttaat gttatctaaa aattgaagag ctgagcttgt     180
tgtattatta aatatcttgt cgtttctttc tttctgtata acctacgtgc aagcaaacca     240
aatcatcaac ataaatgagc ggcgggattt tgaaacacct tctaaacaac ttttttttcta     300 aataaaactt aatgaatgtt tccttttttg aatctttaac aaaaacactt agaacacttg     360
ttaatagtaa aaaatgaaga atataatttg tatttttatta aaatttacta aaaatagtat     420
gatcctcctt tagattgagt ccatataaga tgtcccgtaa gtttaaatat aaaaatcatg     480
gtttggctct ctctatcggg aaaccaaata tgtaaaattg attttgccat atttgtccga     540
tgcttattga aattgatttt tatctctata attatataac ttgaagttag aacttagaac     600
tgcagctttt aatttttaat atgattttta tactcaaatt tagcgttcaa ggcacgcgga     660
catgaatata tttaaatata actaattcac atttaaccca tttttaacta aatcatttta     720
tttgaaaaaa aatttgttgg caaaactaaa catgcactaa accaagttgt ttggcctccg     780
gtggaaagga gctctttcca aggatgtatc cggaaaatac cggactcgat tcacagaggg     840
aacaacgctt gaccaatttg catgagccag attagtcacc aacctttggt gggtcgaaaa     900
ctggtgcaaa agccaaaaaa tccattaaaa aaactaaaca cgcactaaat atttccaact     960
aaagtattag tattatttaa aaaaaaaaca aaaactatat tgtaaaacaa atagtagtat    1020
tatttagtcc ggattctaga atggcgtctt gagactgaat tgtttaatat taaacaaata    1080
aaataaaaaa tgagagactg caacataatt tcctcttctt ttttgggttt gcatttgatc    1140
gtgtaaaaga gaaatctaga tacaagaata cgcagatttt gaatatattg ccatagcttt    1200
```

-continued

```
tgtggttatt tgaatagtat atcaggaatt ttgaaatttg actggtctta gaggagataa       1260
aagaagaaaa aaaaaatagt atatcaagaa ttttgtgaac ccaaataatt tttttcttta       1320
aaattcatat ctcaatgtga ataataaaat ggttccaaca acctgatatt agttagtcat       1380
catctttatc taattagcaa tctaaagtcc aaacaatact gtaccaaaaa aagtctaaat       1440
aatacaactt cagttcctat aaatactagc cataactaca ttcataaacc acacattacg       1500
accattattt gttatttctt acctagcatt ttaatacatt ataccatcat g                1551

<210> SEQ ID NO 2
<211> LENGTH: 3753
<212> TYPE: DNA
<213> ORGANISM: Medicago truncatula

<400> SEQUENCE: 2
ctcgatcaat agttcaaacc aagaaaaca aaatgaatt caagaattag ccaaagccca          60
aacacatata gggattaagc caccaattat gataaaaaaa aaaaagaag acttttttgc        120 attcagtcat cgatagaaaa tgagcttaat gttatctaaa aattgaagag ctgagcttgt       180
tgtattatta aatatcttgt cgtttctttc tttctgtata acctacgtgc aagcaaacca       240
aatcatcaac ataaatgagc ggcgggattt tgaaacacct tctaaacaac tttttttcta       300
aataaaactt aatgaatgtt tccttttttg aatcttaaac aaaaacactt agaacacttg       360
ttaatagtaa aaatgaaga ataaatttg tattttatta aaatttacta aaaatagtat         420
gatcctcctt tagattgagt ccatataaga tgtcccgtaa gtttaaatat aaaaatcatg       480
gtttggctct ctctatcggg aaaccaaata tgtaaaattg atttgccat atttgtccga        540 tgcttattga aattgatttt tatctctata attatataac ttgaagttag aacttagaac      600
tgcagctttt aattttttaat atgatttta tactcaaatt tagcgttcaa ggcacgcgga       660
catgaatata tttaaatata actaattcac atttaaccca ttttttaacta aatcattta       720 tttgaaaaaa aatttgttgg caaaactaaa catgcactaa accaagttgt ttggcctccg       780
gtggaaagga gctcttttcca aggatgtatc cggaaaatac cggactcgat tcacagaggg      840
aacaacgctt gaccaatttg catgagccag attagtcacc aacctttggt gggtcgaaaa       900
ctggtgcaaa agccaaaaaa tccattaaaa aaactaaaca cgcactaaat atttccaact       960
aaagtattag tattatttaa aaaaaaaaca aaaactatat tgtaaaacaa atagtagtat       1020
tatttagtcc ggattctaga atggcgtctt gagactgaat tgtttaatat taaacaaata      1080
aaataaaaaa tgagagactg caacataatt tcctcttctt ttttgggttt gcatttgatc      1140
gtgtaaaaga gaaatctaga tacaagaata cgcagatttt gaatatattg ccatagcttt      1200
tgtggttatt tgaatagtat atcaggaatt ttgaaatttg actggtctta gaggagataa      1260
aagaagaaaa aaaaaatagt atatcaagaa ttttgtgaac ccaaataatt tttttcttta      1320
aaattcatat ctcaatgtga ataataaaat ggttccaaca acctgatatt agttagtcat      1380
catctttatc taattagcaa tctaaagtcc aaacaatact gtaccaaaaa aagtctaaat      1440
aatacaactt cagttcctat aaatactagc cataactaca ttcataaacc acacattacg      1500
accattattt gttatttctt acctagcatt ttaatacatt ataccatcat gggtgtgttc      1560
aattttgagg atgaaaccac ctctaatgta gctcctgcta cactttacaa agctctagtt      1620
acagattctg ataaccttat cccaaaggtt attgatgtca tcaagagtgt tgaaattgtt      1680
gaaggcaacg gtggcgccgg aaccatcaag aaacttactt tgttgaaggt tcggtataaa      1740
tatatttatt ttacttttat tgtcaaatat taataattag ttgttacgtt agtgtttaaa      1800
```

-continued

```
aaaattatgt tttcgacatc gagtctaagt tcagtatgaa ctatacctag taatgctgat    1860
gatgtttgtg attgtgaaac ggatcaatat gcagatggtg agaccaagca ctgatgaatc    1920
ccctaatgat ttttatcaaa atcattaagt taaggtagat acacatcttg tcatatgatc    1980
aaatggtttc gccaaaaatc aataatcaga caacaaaatg tgcgaactcg atattttaca    2040
cgactctctt taccaattct gccccgaatt acacttaaaa cgactcaaca gcttaacgtt    2100
ggcttgccac gccttacttg actgtaaaac tctcactctt accgaacttg gccgtaaccc    2160
gccaaccaaa gcgagaacaa aacataacat caaacgaatc gaccgattgt taggtaatcg    2220
tcacctccac aaagagcgac tcgctgtata ccgttggcat gctagcttta tctgttcggg    2280
caatacgatg cccattgtac ttgttgactg gtctgatatc cgtgagcaaa aacggcttat    2340
ggtattgcga gcttcagtcg cactacacgg tcgttctgtt actctttatg agaaagcgtt    2400
cccgctttca gagcaatgtt caaagaaagc tcatgaccaa tttctagccg accttgcgag    2460
cattctaccg agtaacacca caccgctcat tgtcagtgat gctggctttta aagtgccatg    2520 gtataaatcc gttgagaagc tgggttggta ctggttaagt cgagtaagag gaaaagtaca    2580
atatgcagac ctaggagcgg aaaactggaa acctatcagc aacttacatg atatgtcatc    2640
tagtcactca aagactttag gctataagag gctgactaaa agcaatccaa tctcatgcca    2700
aattctattg tataaatctc gctctaaagg ccgaaaaaat cagcgctcga cacggactca    2760
ttgtcaccac ccgtcaccta aaatctactc agcgtcggca aaggagccat ggattctagc    2820
aactaactta cctgttgaaa ttcgaacacc caaacaactt gttaatatct attcgaagcg    2880
aatgcagatt gaagaaacct tccgagactt gaaaagtcct gcctacggac taggcctacg    2940
ccatagccga acgagcagct cagagcgttt tgatatcatg ctgctaatcg ccctgatgct    3000
tcaactaaca tgttggcttg cgggcgttca tgctcagaaa caaggttggg acaagcactt    3060
ccaggctaac acagtcagaa atcgaaacgt actctcaaca gttcgcttag gcatggaagt    3120
tttgcggcat tctggctaca caataacaag ggaagactta ctcgtggctg caaccctact    3180
agctcaaaat ttattcacac atggttacgc tttggggaaa ttatgagggg atctctcagg    3240
accaagcatg tgttacacaa agtggagtta gtagatgatg ctaacttggc ttacaactac    3300
agcattgttg gaggtgttgg ccttccagac acaatagaga agatttcatt ttgaggctaa    3360
attgtctgca ggtccaaatg gaggatccac tagttctaga gcggccgcca ccgcggtgga    3420
gctccaattc gccctatagt gagtcgtatt acgcgcgctc actggccgtc gttttacaac    3480
gtcgtgactg ggaaaaccct ggcgttaccc aacttaatcg ccttgcagca catccccctt    3540
tcgccagctg gcgtaatagc gaagaggccc gcaccgatcg cccttcccaa cagttgcgca    3600
gcctgaatgg cgaatgggac gcgccctgta gcggcgcatt aagcgcggcg ggtgtggtgg    3660
ttacgcgcag cgtgaccgct acacttgcca gcgccctagc gcccgctcct ttcgctttct    3720 tcccttcct ttctcgccac gttcgccggc ttt    3753
```

<210> SEQ ID NO 3
<211> LENGTH: 716
<212> TYPE: DNA
<213> ORGANISM: Medicago truncatula

<400> SEQUENCE: 3

```
ttcattattt ctttcttaca ctagcattat aattcatcat gggtgtcatc aattttgagg     60
aagaaaccac ctctgttgta gctccagcta cacttcacaa agcttttgtt acagatgctg    120
```

```
acaaccttat cccaaaggtt attgatgtca tcaaaagtat tgacattgtt gaaggaaatg      180
gtggcgccgg aaccatcaag aaactcactt tcgttgaaga tggtgaaacc aagtatgatt      240
tacacaaagt ggagttagta gatgatgcta actgggctta caactacagc attgttggag      300
gtgatagtct tccagacaca gtagagaaga tttcatttga agctaaactg tctgcaggtc      360
caaatggagg atccattgca aaacttagtg tgaaatactt tacaaaagga gatgttactc      420
caagtgaaga ggaactcaag agtggcaaag ctaagggtga tggtcttttc aaggcccttg      480
agggttactg tttggctaat cctgattaca actaaagcat ataattaaat gcttattcat      540
ggtgtgatgt gacacaggat aagctatatc cagtttgctt aatttgggta ccaatgtaat      600
tctctatttt tcccccttc cttttggtaa ggaagtttga gtgtgagatt gtaagtcatg       660
agtgcctccc ttcaaaacat tgtcagcttt ttttaataaa gagattgtta ctattt         716
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
agaggcgact tccattgtag c                                                21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
taggaaaggg aaaagaaaga aaaa                                             24

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tttaagcttc tcgatcaata gttcaaacc                                        29

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ggatccatgg atggtataat gtattaaaat gcta                                  34

<210> SEQ ID NO 8
<211> LENGTH: 424
<212> TYPE: DNA
<213> ORGANISM: Medicago truncatula

<400> SEQUENCE: 8

-continued

```
ctcgatcaat agttcaaacc aaagaaaaca aaaatgaatt caagaattag ccaaagccca    60
aacacatata gggattaagc caccaattat gataaaaaaa aaaaaagaag acttttttgc   120
attcagtcat cgatagaaaa tgagcttaat gttatctaaa aattgaagag ctgagcttgt   180
tgtattatta aatatcttgt cgtttctttc tttctgtata acctacgtgc aagcaaacca   240
aatcatcaac ataaatgagc ggcgggattt tgaaacacct tctaaacaac tttttttcta   300
aataaaactt aatgaatgtt tccttttttg aatctttaac aaaaacactt agaacacttg   360
ttaatagtaa aaaatgaaga atataaatttg tattttatta aaatttacta aaaatagtat   420
gatc                                                              424
```

<210> SEQ ID NO 9
<211> LENGTH: 715
<212> TYPE: DNA
<213> ORGANISM: Medicago truncatula

<400> SEQUENCE: 9

```
ctcgatcaat agttcaaacc aaagaaaaca aaaatgaatt caagaattag ccaaagccca    60
aacacatata gggattaagc caccaattat gataaaaaaa aaaaaagaag acttttttgc   120
attcagtcat cgatagaaaa tgagcttaat gttatctaaa aattgaagag ctgagcttgt   180
tgtattatta aatatcttgt cgtttctttc tttctgtata acctacgtgc aagcaaacca   240
aatcatcaac ataaatgagc ggcgggattt tgaaacacct tctaaacaac tttttttcta   300
aataaaactt aatgaatgtt tccttttttg aatctttaac aaaaacactt agaacacttg   360
ttaatagtaa aaaatgaaga atataaatttg tattttatta aaatttacta aaaatagtat   420
gatcctcctt tagattgagt ccatataaga tgtcccgtaa gtttaaatat aaaaatcatg   480
gtttggctct ctctatcggg aaaccaaata tgtaaaattg attttgccat atttgtccga   540
tgcttattga aattgatttt tatctctata attatataac ttgaagttag aacttagaac   600
tgcagctttt aattttttaat atgattttta tactcaaatt tagcgttcaa ggcacgcgga   660
catgaatata tttaaatata actaattcac atttaaccca ttttttaacta aatca        715
```

<210> SEQ ID NO 10
<211> LENGTH: 1019
<212> TYPE: DNA
<213> ORGANISM: Medicago truncatula

<400> SEQUENCE: 10

```
ctcgatcaat agttcaaacc aaagaaaaca aaaatgaatt caagaattag ccaaagccca    60
aacacatata gggattaagc caccaattat gataaaaaaa aaaaaagaag acttttttgc   120
attcagtcat cgatagaaaa tgagcttaat gttatctaaa aattgaagag ctgagcttgt   180
tgtattatta aatatcttgt cgtttctttc tttctgtata acctacgtgc aagcaaacca   240
aatcatcaac ataaatgagc ggcgggattt tgaaacacct tctaaacaac tttttttcta   300
aataaaactt aatgaatgtt tccttttttg aatctttaac aaaaacactt agaacacttg   360
ttaatagtaa aaaatgaaga atataaatttg tattttatta aaatttacta aaaatagtat   420
gatcctcctt tagattgagt ccatataaga tgtcccgtaa gtttaaatat aaaaatcatg   480
gtttggctct ctctatcggg aaaccaaata tgtaaaattg attttgccat atttgtccga   540
tgcttattga aattgatttt tatctctata attatataac ttgaagttag aacttagaac   600
tgcagctttt aattttttaat atgattttta tactcaaatt tagcgttcaa ggcacgcgga   660
```

```
catgaatata tttaaatata actaattcac atttaaccca tttttaacta aatcatttta        720
tttgaaaaaa aatttgttgg caaaactaaa catgcactaa accaagttgt ttggcctccg        780
gtggaaagga gctctttcca aggatgtatc cggaaaatac cggactcgat tcacagaggg        840
aacaacgctt gaccaatttg catgagccag attagtcacc aacctttggt gggtcgaaaa        900
ctggtgcaaa agccaaaaaa tccattaaaa aaactaaaca cgcactaaat atttccaact        960
aaagtattag tattatttaa aaaaaaaaca aaaactatat tgtaaaacaa atagtagta       1019
```

<210> SEQ ID NO 11
<211> LENGTH: 1290
<212> TYPE: DNA
<213> ORGANISM: Medicago truncatula

<400> SEQUENCE: 11

```
ctcgatcaat agttcaaacc aaagaaaaca aaatgaatt caagaattag ccaaagccca         60
aacacatata gggattaagc caccaattat gataaaaaaa aaaaagaag acttttttgc        120 attcagtcat cgatagaaaa tgagcttaat gttatctaaa aattgaagag ctgagcttgt        180
tgtattatta aatatcttgt cgtttctttc tttctgtata acctacgtgc aagcaaacca        240
aatcatcaac ataaatgagc ggcgggattt tgaaacacct tctaaacaac tttttttcta        300
aataaaactt aatgaatgtt tcctttttg aatctttaac aaaaacactt agaacacttg        360
ttaatagtaa aaaatgaaga atataatttg tattttatta aaatttacta aaaatagtat        420
gatcctcctt tagattgagt ccatataaga tgtcccgtaa gtttaaatat aaaaatcatg        480
gtttggctct ctctatcggg aaaccaaata tgtaaaattg attttgccat atttgtccga        540
tgcttattga aattgatttt tatctctata attatataac ttgaagttag aacttagaac        600
tgcagctttt aattttttaat atgattttta tactcaaatt tagcgttcaa ggcacgcgga        660
catgaatata tttaaatata actaattcac atttaaccca tttttaacta aatcatttta        720
tttgaaaaaa aatttgttgg caaaactaaa catgcactaa accaagttgt ttggcctccg        780
gtggaaagga gctctttcca aggatgtatc cggaaaatac cggactcgat tcacagaggg        840
aacaacgctt gaccaatttg catgagccag attagtcacc aacctttggt gggtcgaaaa        900
ctggtgcaaa agccaaaaaa tccattaaaa aaactaaaca cgcactaaat atttccaact        960
aaagtattag tattatttaa aaaaaaaaca aaaactatat tgtaaaacaa atagtagtat       1020
tatttagtcc ggattctaga atggcgtctt gagactgaat tgtttaatat taaacaaata       1080
aaataaaaaa tgagagactg caacataatt tcctcttctt ttttgggttt gcatttgatc       1140
gtgtaaaaga gaaatctaga tacaagaata cgcagatttt gaatatattg ccatagcttt       1200
tgtggttatt tgaatagtat atcaggaatt ttgaaatttg actggtctta gaggagataa       1260
aagaagaaaa aaaaaatagt atatcaagaa                                       1290
```

<210> SEQ ID NO 12
<211> LENGTH: 1435
<212> TYPE: DNA
<213> ORGANISM: Medicago truncatula

<400> SEQUENCE: 12

```
ctcgatcaat agttcaaacc aaagaaaaca aaatgaatt caagaattag ccaaagccca         60
aacacatata gggattaagc caccaattat gataaaaaaa aaaaagaag acttttttgc        120 attcagtcat cgatagaaaa tgagcttaat gttatctaaa aattgaagag ctgagcttgt        180
tgtattatta aatatcttgt cgtttctttc tttctgtata acctacgtgc aagcaaacca        240
```

-continued

| | |
|---|---|
| aatcatcaac ataaatgagc ggcgggattt tgaaacacct tctaaacaac ttttttttcta | 300 |
| aataaaactt aatgaatgtt tccttttttg aatcttttaac aaaaacactt agaacacttg | 360 |
| ttaatagtaa aaaatgaaga atataaattg tattttatta aaatttacta aaaatagtat | 420 |
| gatcctcctt tagattgagt ccatataaga tgtcccgtaa gtttaaatat aaaaatcatg | 480 |
| gtttggctct ctctatcggg aaaccaaata tgtaaaattg attttgccat atttgtccga | 540 |
| tgcttattga aattgatttt tatctctata attatataac ttgaagttag aacttagaac | 600 |
| tgcagctttt aattttttaat atgattttta tactcaaatt tagcgttcaa ggcacgcgga | 660 |
| catgaatata tttaaatata actaattcac atttaaccca ttttttaacta aatcatttta | 720 |
| tttgaaaaaa aatttgttgg caaaactaaa catgcactaa accaagttgt ttggcctccg | 780 |
| gtggaaagga gctctttcca aggatgtatc cggaaaatac cggactcgat tcacagaggg | 840 |
| aacaacgctt gaccaatttg catgagccag attagtcacc aacctttggt gggtcgaaaa | 900 |
| ctggtgcaaa agccaaaaaa tccattaaaa aaactaaaca cgcactaaat atttccaact | 960 |
| aaagtattag tattatttaa aaaaaaaaca aaaactatat gtaaaacaa atagtagtat | 1020 |
| tatttagtcc ggattctaga atggcgtctt gagactgaat tgtttaatat taaacaaata | 1080 |
| aaataaaaaa tgagagactg caacataatt tcctcttctt ttttgggttt gcatttgatc | 1140 |
| gtgtaaaaga gaaatctaga tacaagaata cgcagatttt gaatatattg ccatagcttt | 1200 |
| tgtggttatt tgaatagtat atcaggaatt ttgaaatttg actggtctta gaggagataa | 1260 |
| aagaagaaaa aaaaaatagt atatcaagaa ttttgtgaac ccaaataatt ttttttcttta | 1320 |
| aaattcatat ctcaatgtga ataataaaat ggttccaaca acctgatatt agttagtcat | 1380 |
| catctttatc taattagcaa tctaaagtcc aaacaatact gtaccaaaaa aagtc | 1435 |

<210> SEQ ID NO 13
<211> LENGTH: 1118
<212> TYPE: DNA
<213> ORGANISM: Medicago truncatula

<400> SEQUENCE: 13

| | |
|---|---|
| ctcctttaga ttgagtccat ataagatgtc ccgtaagttt aaatataaaa atcatggttt | 60 |
| ggctctctct atcgggaaac caaatatgta aaattgattt tgccatattt gtccgatgct | 120 |
| tattgaaatt gattttttatc tctataatta tataacttga agttagaact tagaactgca | 180 |
| gcttttaatt tttaatatga ttttatact caaatttagc gttcaaggca cgcggacatg | 240 |
| aatatattta aatataacta attcacattt aacccatttt taactaaatc attttatttg | 300 |
| aaaaaaaatt tgttggcaaa actaaacatg cactaaacca agttgtttgg cctccggtgg | 360 |
| aaaggagctc tttccaagga tgtatccgga aaataccgga ctcgattcac agagggaaca | 420 |
| acgcttgacc aatttgcatg agccagatta gtcaccaacc tttggtgggt cgaaaactgg | 480 |
| tgcaaaagcc aaaaaatcca ttaaaaaaac taaacacgca ctaaatattt ccaactaaag | 540 |
| tattagtatt atttaaaaaa aaacaaaaa ctatattgta aaacaaatag tagtattatt | 600 |
| tagtccggat tctagaatgg cgtcttgaga ctgaattgtt taatattaaa caaataaaat | 660 |
| aaaaaatgag agactgcaac ataatttcct cttcttttttt gggtttgcat tgatcgtgt | 720 |
| aaaagagaaa tctagataca agaatacgca gattttgaat atattgccat agcttttgtg | 780 |
| gttatttgaa tagtatatca ggaattttga aatttgactg gtcttagagg agataaaaga | 840 |
| agaaaaaaaa aatagtatat caagaatttt gtgaacccaa ataatttttt tctttaaaat | 900 |

```
tcatatctca atgtgaataa taaaatggtt ccaacaacct gatattagtt agtcatcatc      960
tttatctaat tagcaatcta aagtccaaac aatactgtac caaaaaaagt ctaaataata     1020
caacttcagt tcctataaat actagccata actacattca taaaccacac attacgacca     1080
ttatttgtta tttcttacct agcattttaa tacattat                             1118

<210> SEQ ID NO 14
<211> LENGTH: 827
<212> TYPE: DNA
<213> ORGANISM: Medicago truncatula

<400> SEQUENCE: 14
ttttatttga aaaaaattt gttggcaaaa ctaaacatgc actaaaccaa gttgtttggc       60
ctccggtgga aaggagctct ttccaaggat gtatccggaa ataccggac tcgattcaca     120 gagggaacaa cgcttgacca atttgcatga gccagattag tcaccaacct ttggtgggtc     180
gaaaactggt gcaaaagcca aaaatccat taaaaaaact aaacacgcac taaatatttc     240
caactaaagt attagtatta tttaaaaaaa aacaaaaac tatattgtaa acaaatagt      300 agtattattt agtccggatt ctagaatggc gtcttgagac tgaattgttt aatattaaac     360
aaataaaata aaaatgaga gactgcaaca taatttcctc ttcttttttg ggtttgcatt     420
tgatcgtgta aagagaaat ctagatacaa gaatacgcag attttgaata tattgccata     480
gcttttgtgg ttatttgaat agtatatcag gaattttgaa atttgactgg tcttagagga     540
gataaaagaa gaaaaaaaaa atagtatatc aagaattttg tgaacccaaa taatttttt     600 ctttaaaatt catatctcaa tgtgaataat aaaatggttc caacaacctg atattagtta     660
gtcatcatct ttatctaatt agcaatctaa agtccaaaca atactgtacc aaaaaaagtc     720
taaataatac aacttcagtt cctataaata ctagccataa ctacattcat aaaccacaca     780
ttacgaccat tatttgttat ttcttaccta gcattttaat acattat                  827

<210> SEQ ID NO 15
<211> LENGTH: 523
<212> TYPE: DNA
<213> ORGANISM: Medicago truncatula

<400> SEQUENCE: 15
ttatttagtc cggattctag aatggcgtct tgagactgaa ttgtttaata ttaaacaaat      60
aaaataaaaa atgagagact gcaacataat tcctcttct tttttgggtt tgcatttgat    120
cgtgtaaaag agaaatctag atacaagaat acgcagattt tgaatatatt gccatagctt     180
ttgtggttat ttgaatagta tatcaggaat tttgaaattt gactggtctt agaggagata     240
aaagaagaaa aaaaaatag tatatcaaga attttgtgaa cccaaataat tttttctttt     300
aaaattcata tctcaatgtg aataataaaa tggttccaac aacctgatat tagttagtca     360
tcatctttat ctaattagca atctaaagtc caaacaatac tgtaccaaaa aaagtctaaa     420
taatacaact tcagttccta taaatactag ccataactac attcataaac cacacattac     480
gaccattatt tgttatttct tacctagcat tttaatacat tat                      523

<210> SEQ ID NO 16
<211> LENGTH: 252
<212> TYPE: DNA
<213> ORGANISM: Medicago truncatula

<400> SEQUENCE: 16
ttttgtgaac ccaaataatt ttttctttta aaattcatat ctcaatgtga ataataaaat      60
```

```
ggttccaaca acctgatatt agttagtcat catctttatc taattagcaa tctaaagtcc      120
aaacaatact gtaccaaaaa aagtctaaat aatacaactt cagttcctat aaatactagc      180
cataactaca ttcataaacc acacattacg accattattt gttatttctt acctagcatt      240
ttaatacatt at                                                         252

<210> SEQ ID NO 17
<211> LENGTH: 107
<212> TYPE: DNA
<213> ORGANISM: Medicago truncatula

<400> SEQUENCE: 17
taaataatac aacttcagtt cctataaata ctagccataa ctacattcat aaaccacaca      60
ttacgaccat tatttgttat ttcttaccta gcattttaat acattat                   107

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 18
actgtaccaa aaaaagctta aataa                                           25

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19
aatagtatat caagcttttt gtgaac                                          26

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 20
acaaatagaa gctttattta gtccg                                           25

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 21
cccattttta actaaagctt tttatt                                          26

<210> SEQ ID NO 22
<211> LENGTH: 26
<212> TYPE: DNA
<213> ORGANISM: Artificial Sequence
<220> FEATURE:
```

-continued

```
<223> OTHER INFORMATION: Description of Artificial Sequence:  Synthetic
      Primer

<400> SEQUENCE: 22
agtaagcttc tcctttagat tgagtc                                           26

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 23
ggccatggat aatgtattaa aatgctaggt                                       30
```

US 7,056,743 B2

MTHP PROMOTER ELEMENT

This application claims the priority of U.S. Provisional Patent Application Ser. No. 60/459,903, filed Apr. 2, 2003.

BACKGROUND OF THE INVENTION

1. Field of the Invention

The invention relates generally to the field of molecular biology. More specifically, it relates to nucleic acid sequences for the expression of recombinant nucleic acid sequences in transgenic cells and methods related thereto.

2. Description of the Related Art

An important aspect in the production of genetically engineered plants is obtaining sufficient levels of transgene expression in the appropriate plant tissues. In this respect, the selection of promoters for directing expression of a given transgene is crucial. Promoters which are useful for plant transgene expression include those that are inducible, viral, synthetic, and constitutive as described (Poszkowski et al., 1989; Odell et al., 1985).

A number of plant promoters have been described with various expression characteristics. Examples of some constitutive promoters which have been described include the rice actin 1 (Wang et al., 1992; U.S. Pat. No. 5,641,876), CaMV 35S (Odell et al., 1985), CaMV 19S (Lawton et al., 1987), Ti plasmid nopaline synthase (nos, Ebert et al., 1987), alcohol dehydrogenase (Adh, Walker et al., 1987), maize ubiquitin promoter (Christensen and Quail, 1996), and sucrose synthase promoters (Yang and Russell, 1990).

Examples of tissue specific promoters which have been described include the lectin (Vodkin et al., 1983; Lindstrom et al., 1990), corn alcohol dehydrogenase 1 (Vogel et al., 1989; Dennis et al., 1984), corn light harvesting complex (Simpson, 1986; Bansal et al., 1992), corn heat shock protein (Odell et al., 1985; Rochester et al., 1986), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), truncated CaMV 35s (Odell et al., 1985), potato patatin (Wenzler et al., 1989), root cell (Conkling et al., 1990), cab (Sullivan et al., 1989), PEPCase (Hudspeth and Grula, 1989), R gene complex-associated promoters (Chandler et al., 1989), and chalcone synthase promoters (Franken et al., 1991).

Inducible promoters which have been described include ABA- and turgor-inducible promoters, the promoter of the auxin-binding protein gene (Schwob et al., 1993), the UDP glucose flavonoid glycosyl-transferase gene promoter (Ralston et al., 1988); the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989).

Both the CaMV 19S and 35S promoters have been used for constitutive expression of transgenes in plants. The 35S promoter is considered to be one of the strongest promoters in plants. (Guilley et al., 1982). The 35S promoter mediates expression of foreign genes in almost any organ of the plant and is the most commonly utilized promoter for the constitutive expression of any gene of interest in plants (Odell et al., 1985; Jefferson et al., 1987).

Although prior studies have provided a number of useful tools for the generation of transgenic plants, there is still a great need in the art for novel sequences that function as promoter elements for the high-level expression of transgenes. New promoters, especially promoters that will express transgenes at high levels, are needed. In addition to providing valuable new tools for the expression of transgenes, a wider range of effective promoters also would make it possible to introduce multiple transgenes into a cell while still avoiding the risk of DNA sequence homology dependent transgene inactivation. Therefore, there is a great need in the art for the identification of novel promoter elements for expression of transgenes in eukaryotes.

SUMMARY OF THE INVENTION

In one aspect, the invention provides an isolated nucleic acid sequence comprising a MtHP promoter, the promoter comprising the nucleic acid sequence of SEQ ID NO:1 or a fragment thereof having promoter activity. In certain embodiments of the invention, the isolated nucleic acid sequence may be linked to any desired sequences, including an enhancer and a coding sequence. In one embodiment of the invention, the isolated nucleic acid sequence is further defined as comprising the nucleic acid sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In another aspect, the invention provides a transformation construct comprising: (a) an isolated nucleic acid sequence comprising a MtHP promoter, the promoter comprising the nucleic acid sequence of SEQ ID NO:1 or a fragment thereof having promoter activity; and (b) a heterologous coding sequence operably linked to said MtHP promoter. In certain embodiments of the invention, the coding sequence is operably linked to a terminator. In further embodiments of the invention, the construct may comprise any further additional desired component, including a selectable marker, at least a second promoter, at least a second heterologous coding sequence operably linked to said second promoter and/or a screenable marker. In one embodiment of the invention, the isolated nucleic acid sequence comprises the nucleic acid sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In yet another aspect, the invention provides a plant transformed with a selected DNA comprising a MtHP promoter operably linked to a heterologous coding sequence, wherein said promoter comprises the nucleic acid sequence of SEQ ID NO:1 or a fragment thereof having promoter activity. The plant may be any type of plant, including a dicotyledonous plant or a monocotyledonous plant. Examples of dicotyledonous plants include, but are not limited to, tobacco, alfalfa, tomato, potato, soybean, clover, cotton, canola, or sunflower. Examples of monocotyledonous plants include, but are not limited to, wheat, maize, rye, rice, oat, barley, turfgrass, sorghum, millet or sugarcane. In certain embodiments of the invention, the promoter comprises the nucleic acid sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17. In still further embodiments of the invention, derivatives of such a plant are provided, including a cell of the plant, a seed of the plant which seed comprises the selected DNA, and a progeny plant of any generation of the plant which comprises said selected DNA.

In still yet another aspect, the invention provides a method of expressing a polypeptide in a plant cell comprising the steps of: (a) obtaining a construct comprising a MtHP promoter operably linked to a heterologous coding sequence, wherein said promoter comprises the nucleic acid sequence of SEQ ID NO:1 or a fragment thereof having promoter activity; and (b) transforming a recipient plant cell with the construct, wherein said recipient plant cell expresses said selected polypeptide. The plant used in the method may be any type of plant, including a dicotyledonous plant or a monocotyledonous plant. Examples of dicotyledonous plants include, but are not limited to, tobacco, clover, alfalfa, tomato, potato, soybean, cotton, canola, or sunflower. Examples of monocotyledonous plants include, but are not limited to, wheat, maize, rye, rice, oat, barley, turfgrass, sorghum, millet or sugarcane. In certain embodiments, the promoter may comprise the nucleic acid sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In still yet another aspect, the invention provides a method of producing a plant transformed with a selected DNA comprising a MtHP promoter operably linked to a heterologous coding sequence, wherein said promoter comprises the nucleic acid sequence of SEQ ID NO:1 or a fragment thereof having promoter activity, comprising: (a) obtaining a first plant comprising said selected DNA; (b) crossing said first plant to a second plant lacking said selected DNA; and (c) obtaining at least a first progeny plant resulting from said crossing, wherein said progeny plant has inherited said selected DNA. The plant used in the method may be any type of plant, including a dicotyledonous plant or a monocotyledonous plant. Examples of dicotyledonous plants include, but are not limited to, tobacco, alfalfa, tomato, clover, potato, soybean, cotton, canola, or sunflower. Examples of monocotyledonous plants include, but are not limited to, wheat, maize, rye, rice, oat, barley, turfgrass, sorghum, millet or sugarcane. In certain embodiments, the promoter may comprise the nucleic acid sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

FIG. 1: Sequence of a cDNA clone Mt12a obtained by screening a *M. truncatula* cDNA library using the pea RH2 as probe (SEQ ID NO:3).

FIG. 5: Sequence of the 5' region of the genomic clone obtained after screening a *M. truncatula* genomic library using Mt12a as probe (SEQ ID NO:2). Exons are in lowercase letters.

FIG. 7: *M. truncatula* hairy root showing GUS expression after *A. rhizogenes* mediated transformation.

FIG. 9: MtHP full length promoter sequence (SEQ ID NO:1). Deletion segments designed are shown by arrows. Examples of promoter sequences designed are given in SEQ ID NOs:8–17 and SEQ ID NOs:18–23.

FIG. 13: GUS expression in transgenic white clover leaves and transgenic alfalfa calluses.

FIG. 14: GUS expression in transgenic *Arabidopsis* plants carrying deleted MtHP-GUS gene constructs with varying lengths of promoter regions.

DETAILED DESCRIPTION OF THE INVENTION

Figure 2:
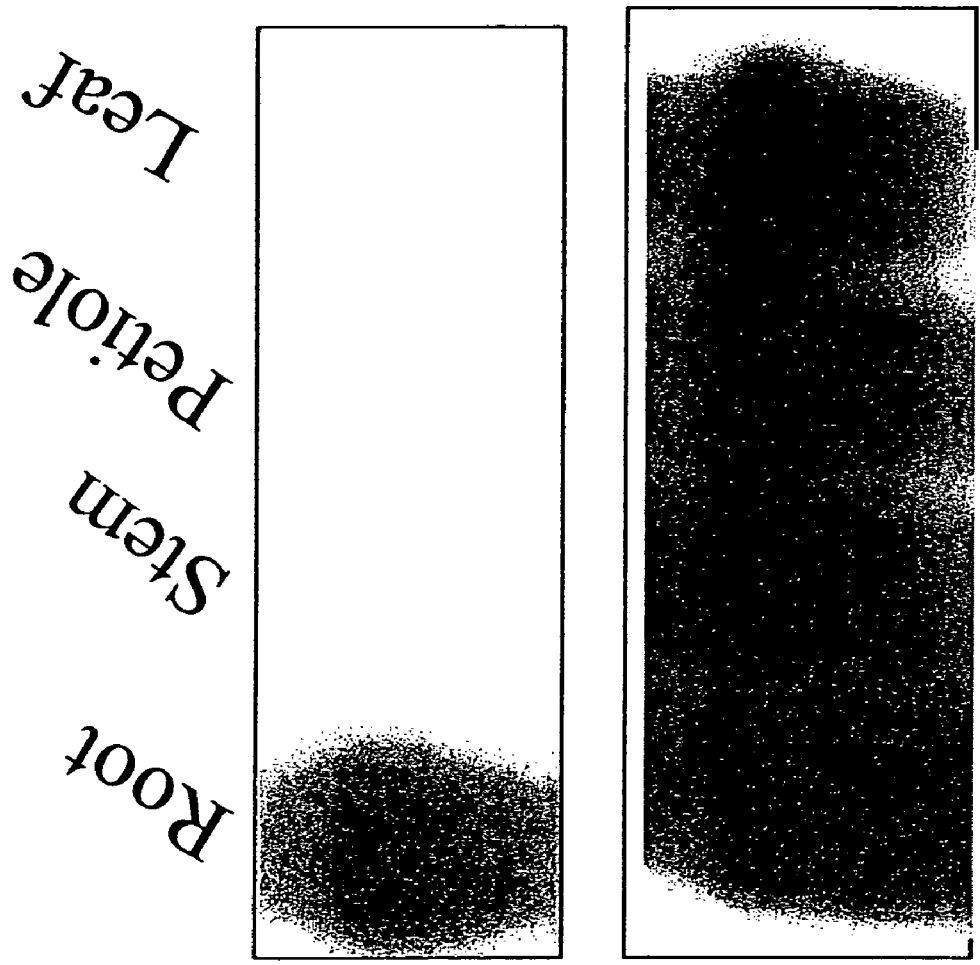
FIG. 2: RNA gel analysis of different *M. truncatula* tissues using Mt12a as probe.

The invention overcomes deficiencies in the prior art by providing novel methods and compositions for the efficient expression of transgenes in plants. In particular, the invention provides a promoter initially isolated from *Medicago truncatula* and designated the MtHP promoter. The MtHP promoter described herein represents a constitutive promoter giving high-level expression in plants. In planta expression studies yielded expression levels exceeding that of the CaMV 35S promoter. The promoter therefore represents a significant advance in the art. By operably linking the identified MtHP promoter to one or more selected coding sequences, high-level expression of that transgene may therefore be obtained. Potentially any coding sequence could be expressed with the MtHP promoter.

One aspect of the current invention comprises a MtHP promoter sequence exemplified by SEQ ID NO:1 and fragments thereof having promoter activity. In addition to the unmodified MtHP promoter sequence, the current invention includes derivatives of this sequence and compositions made therefrom. In particular, the present disclosure provides the teaching for one of skill in the art to make and use derivatives of the MtHP promoter. For example, the disclosure provides the teaching for one of skill in the art to create fragments of the MtHP promoter which comprise promoter activity. Examples of such fragments that have been designed are given in SEQ ID NOs:8–17. FIG. 9 also shows examples of portions of the MtHP promoter sequence that one could delete. As the MtHP promoter sequence has been provided, one of skill in the art may delete any non-essential elements as desired.

In certain aspects of the invention, promoter sequences comprising at least about 40, 60, 80, 100, 125, 150, 175, 200 or about 225 contiguous base pairs of SEQ ID NO:1 are provided, as are constructs comprising these sequences operably linked to a heterologous coding sequence. Specific promoter segments contemplated for use as promoters include segments given in SEQ ID NOs:8–17, as well as those defined by FIG. 9.

Also provided by the invention are sequences which have been derived from a MtHP promoter region. An efficient means for preparing such derivatives comprises introducing mutations into the sequences of the invention, for example, the sequence given in SEQ ID NO:1. Such mutants may potentially have enhanced or altered function relative to the native sequence or alternatively, may be silent with regard to function. Mutagenesis can be carried out at random and the mutagenized sequences screened for function in a trial and error procedure. Alternatively, particular sequences which provide the MtHP promoter with desirable expression characteristics could be identified and these or similar sequences introduced into other related or non-related sequences via mutation- Similarly, non-essential elements may be deleted without significantly altering the function of the elements. It further is contemplated that one could mutagenize these sequences in order to enhance their utility in expressing tranagenes in a particular species.

The means for mutagenizing a DNA segment encoding a MtHP promoter sequence of the current invention are well-known to those of skill in the art. Mutagenesis may be performed in accordance with any of the techniques known in the art, such as, but not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis which eliminates the step of transferring the gene of interest from a plasmid to a phage.

Site-directed mutagenesis typically is performed by first obtaining a single-stranded vector or melting apart of two strands of a double-stranded vector which includes a DNA sequence which comprises the MtHP promoter. An oligonucleotide primer bearing the desired mutated sequence is prepared, generally synthetically. This primer is then annealed with the single-stranded vector, and subjected to DNA polymerizing enzymes such as the E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and cells are selected which include recombinant vectors bearing the mutated sequence arrangement. Vector DNA can then be isolated from these cells and used for transformation. A genetic selection scheme was devised by Kunkel et al. (1987) to enrich for clones incorporating mutagenic oligonucleotides. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase also may be used to incorporate a phosphorylated mutagenic oligonucleotide into an amplified DNA fragment that may then be cloned into an appropriate cloning or expression vector.

The preparation of sequence variants of the selected promoter DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide-directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Ramstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety. A number of template dependent processes are available to amplify the target sequences of interest present in a sample, such methods being well known in the art and specifically disclosed herein below.

An efficient, targeted means for preparing mutagenized promoters relies upon the identification of putative regulatory elements within the target sequence. This can be initiated by comparison with, for example, promoter sequences known to be expressed in a similar manner. Sequences which are shared among elements with similar functions or expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter or intron sequence is provided, any of a number of different functional deletion mutants of the starting sequence could be readily prepared.

As indicated above, deletion mutants of the MtHP promoter also could be randomly prepared and then assayed. With this strategy, a series of constructs are prepared, each containing a different portion of the clone (a subclone), and these constructs are then screened for activity. A suitable means for screening for activity is to attach a deleted promoter construct to a selectable or screenable marker, and to isolate only those cells expressing the marker protein. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous protein.

I. Transformation Constructs

One application of the MtHP promoter will be in the construction of vectors designed for introduction into host cells by genetic transformation. The construction of vectors which may be employed according to the invention will be known to those of skill of the art in light of the present disclosure (see for example, Sambrook et al., 1989; Gelvin et al., 1990). The techniques of the current invention are thus not limited to any particular DNA sequences in conjunction with the MtHP promoter sequences of the invention. For example, the MtHP promoter alone could be transformed into a cell with the goal of enhancing or altering the expression of one or more genes in the host genome.

Transformation vectors can be used to direct the expression of a selected coding region which encodes a particular protein or polypeptide product in a transgenic cell. In certain embodiments, a recipient cell may be transformed with more than one transformation construct. Two or more transgenes can also be introduced in a single transformation event using either distinct selected protein-encoding vectors, or using a single vector incorporating two or more gene coding sequences. Of course, any two or more transgenes of any description may be employed as desired.

Vectors used for transformation may include, for example, plasmids, cosmids, YACs (yeast artificial chromosomes), BACs (bacterial artificial chromosomes) or any other suitable cloning system, and the nucleic acids selected therefrom. It is contemplated that utilization of cloning systems with large insert capacities will allow introduction of large DNA sequences comprising more than one selected gene. Introduction of such sequences may be facilitated by use of bacterial or yeast artificial chromosomes (BACs or YACs, respectively).

Particularly useful for transformation may be expression cassette portions of vectors, isolated away from sequences not essential for expression in plants. DNA segments used for transforming cells will generally comprise the cDNA, gene or genes which one desires to introduced into and have expressed in the host cells. These DNA segments can further include, in addition to a MtHP promoter, structures such as promoters, enhancers, terminators, polylinkers, or even regulatory genes as desired. The DNA segment or gene chosen for cellular introduction may encode a protein which will be expressed in the resultant recombinant cells resulting in a screenable or selectable trait and/or which will impart an improved phenotype to the resulting transgenic cell or an organism. Alternatively, the vector may comprise a coding sequence for a protein or polypeptide which is to be isolated from the transgenic cells or is excreted from the transgenic cells. Exemplary components that may advantageously be used with transformation vectors are as follows.

A. Regulatory Elements

In addition to a MtHP promoter or a derivative thereof, constructs prepared in accordance with the invention may comprise additional desired elements. For example, one aspect of the invention relates to the preparation of transformation constructs comprising the MtHP promoter operably linked to a selected coding region. Additionally, by including an enhancer sequence with such constructs, the expression of the selected protein may be enhanced. Enhancers often are found 5' to the start of transcription in a promoter that functions in eukaryotic cells, but can often be inserted in the forward or reverse orientation 5' or 3' to the coding sequence.

Where an enhancer is used in conjunction with a MtHP promoter for the expression of a selected protein, it will often be preferable to place the enhancer between the promoter and the start codon of the selected coding region. However, one also could use a different arrangement of the enhancer relative to other sequences and potentially still realize the beneficial properties conferred by the enhancer. For example, the enhancer could be placed 5' of the promoter region, within the promoter region, within the coding sequence (including within any intron sequences which may be present), or 3' of the coding region.

It also is contemplated that expression of one or more transgenes may be eliminated upon induction of the MtHP promoter provided herein. In particular, by operably linking the MtHP promoter to a coding sequence in antisense orientation, accumulation of the respective protein encoded by the sense transcript could be eliminated or decreased upon expression with the MtHP promoter.

B. Terminators

Transformation constructs prepared in accordance with the invention will typically include a sequence that acts as a signal to terminate transcription and allow for the polyadenylation of the mRNA produced by coding sequences operably linked to the MtHP or another promoter. The termination sequence is preferably located in the 3' flanking sequence of a coding sequence, which will contain proper signals for transcription termination and polyadenylation. Many such terminator sequences are known to those of skill in the art. In constructing suitable expression constructs, the termination sequences associated known genes from the host organism which are efficiently expressed in particular may be ligated into the expression vector 3' of the heterologous coding sequences to provide polyadenylation and termination of the mRNA.

C. Marker Genes

By employing a selectable or screenable marker gene as, or in addition to, a particular gene of interest, one can provide or enhance the ability to identify transformants. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker genes are known to the art and can be employed in the practice of the invention.

Included within the terms selectable or screenable marker genes also are genes which encode a "secretable marker" whose secretion can be detected as a means of identifying or selecting for transformed cells. Examples include marker genes which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions may be used in connection with the MtHP promoter of the present invention. Examples of selectable markers include neo (Potrykus et al., 1985), which provides kanamycin resistance and can be selected for using kanamycin, G418, paromomycin, etc.; bar, which confers bialaphos or phosphinothricin resistance; a nitrilase such as bxn from *Klebsiella ozaenae* which confers resistance to bromoxynil (Stalker et al., 1988) and a mutant acetolactate synthase (ALS) which confers resistance to imidazolinone, sulfonylurea or other ALS inhibiting chemicals (European Patent Application 154, 204, 1985) and a methotrexate resistant DHFR (Thillet et al., 1988).

Screenable markers that may be employed include a β-glucuronidase (GUS) or uidA gene, isolated from *E. coli*, which encodes an enzyme for which various chromogenic substrates are known; a β-lactamase gene (Sutcliffe, 1978), which encodes an enzyme for which various chromogenic substrates are known (e.g., PADAC, a chromogenic cephalosporin); a β-galactosidase gene, which encodes an enzyme for which there are chromogenic substrates; a luciferase (lux) gene (Ow et al., 1986), which allows for bioluminescence detection or a gene encoding for green fluorescent protein (Sheen et al., 1995; Haseloff et al., 1997; Reichel et al., 1996; Tian et al., 1997; WO 97/41228).

Other screenable markers provide for visible light emission as a screenable phenotype. A screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence. The gene which encodes green fluorescent protein (GFP) is contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell as fluorescence following illumination by particular wavelengths of light.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

D. Other Components

Sequences that are joined to the coding sequence of an expressed gene, which are removed post-translationally from the initial translation product and which facilitate the transport of the protein into or through intracellular or extracellular membranes, are termed transit or signal sequences. By facilitating the transport of the protein into compartments inside and outside the cell, these sequences may increase the accumulation of a gene product protecting the protein from intracellular proteolytic degradation. These sequences also allow for additional mRNA sequences from highly expressed genes to be attached to the coding sequence of the genes. Since mRNA being translated by ribosomes is more stable than naked mRNA, the presence of translatable mRNA 5' of the gene of interest may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

In general embodiments of the invention, a nucleic acid segment encoding a leader peptide sequence upstream and in reading frame with a selected coding sequence is used in recombinant expression of the coding sequence in a host cell. In certain aspects, a leader peptide sequence comprises a signal recognized by a host cell that directs the transport of a polypeptide expressed in accordance with the invention through the outer membrane of a cell or into the periplasmic space. In aspects wherein the secreted product is transported into the extracellular medium, that product may be readily purified from host cells. In some aspects, the leader sequences may be removed by enzymatic cleavage. Such leader peptide sequences and nucleic acids encoding the sequences are known in the art.

Additionally, vectors may be constructed and employed in the intracellular targeting of a specific gene product within the cells of a transgenic organism or in directing a protein to the extracellular environment. This generally will be achieved by joining a DNA sequence encoding a transit or signal peptide sequence to the coding sequence of a particular gene. An intracellular targeting DNA sequence may be operably linked 5' or 3' to the coding sequence depending on the particular targeting sequence. The resultant transit, or signal, peptide will transport the protein to a particular intracellular, or extracellular destination, respectively, and will then be post-translationally removed.

It may also be desired that a transformation construct comprises a bacterial origin of replication. One example of such a origin of replication is a colE1 origin. It also may be desirable to include a bacterial selectable marker in the vector, for example, an ampicillin, tetracyclin, hygromycin, neomycin or chloramphenicol resistance gene (Bolivar et al., 1977). The Ap gene is an example of an *E. coli* marker gene which has been cloned and sequenced and which confers resistance to beta-lactam antibiotics such as ampicillin (nucleotides 4618 to 5478 of GenBank accession number U66885). Constructs comprising such elements may advantageously be propagated in bacterial cells such as *E. coli* cells.

E. Vector Construction

Expression constructs preferably comprise restriction endonuclease sites to facilitate vector construction. Particularly useful are unique restriction endonuclease recognition sites. Examples of such restriction sites include sites for the restriction endonucleases NotI, AatII, SacII and PmeI. Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave DNA molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example. Some restriction endonucleases that may be particularly useful with the current invention include HindIII, PstI, EcoRI, and BamHI.

Some endonucleases create fragments that have blunt ends, that is, that lack any protruding single strands. An alternative way to create blunt ends is to use a restriction enzyme that leaves overhangs, but to fill in the overhangs with a polymerase, such as klenow, thereby resulting in blunt ends. When DNA has been cleaved with restriction enzymes that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease which starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases which may be particularly useful in the present invention include Bal31, SI, and ExoIII. These nucleolytic reactions can be controlled by varying the time of incubation, the temperature, and the enzyme concentration needed to make deletions. Phosphatases and kinases also may be used to control which fragments have ends which can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends they are incubated together with enzymes capable of mediating the ligation of the two DNA molecules. Particularly useful enzymes for this purpose include T4 ligase, *E. coli* ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273, 875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementarity can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in one embodiment of the invention, at least two classes of the vectors used in the present invention are adapted to receive the foreign oligonucleotide fragments in only one orientation. After joining the DNA segment to the vector, the resulting hybrid DNA can then be selected from among the large population of clones or libraries.

F. Utilization of Expression Constructs

Introduction of expression vectors into host cells in accordance with the invention will find use for the introduction of one or more new traits to the host cell. One example of such a trait is the ability to produce a heterologous protein. Potentially any of the many techniques known in the art for introducing the vector DNA may be employed, whereby the host becomes capable of efficient expression of the inserted sequences. Such expression can be obtained by operably linking a promoter, coding sequence and sequence containing transcription termination signals (a "terminator"). That is, the promoter effects proper expression of the protein or, if a signal sequence is present, the signal sequence-protein complex and the terminator effects proper termination of transcription and polyadenylation. In case a signal sequence is used, the signal sequence is linked in the proper reading frame to the protein gene in such a manner that the last codon of the signal sequence is directly linked to the first codon of the gene for the protein. The signal sequence, if present, has its own ATG for translation initiation.

II. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac *et al.*, 1998), and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; *D'Halluin et al.*, 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

III. Production and Characterization of Stably Transformed Plants

After effecting delivery of exogenous DNA to recipient cells, the next steps generally concern identifying the transformed cells and plants grown therefrom. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468; and U.S. Pat. No. 5,508,468; each of the disclosures of which is specifically incorporated herein by reference in its entirety).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In one embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, can then be allowed to mature into plants. Developing plantlets may be transferred to soiless plant growth mix, and hardened, e.g., in an environmentally controlled chamber, for example, at about 85% relative humidity, 600 ppm $CO_2$, and 25–250 microeinsteins $m^{-2} s^{-1}$ of light. Plants are preferably matured either in a growth chamber or greenhouse. Plants can be regenerated from about 6 wk to 10 months after a transformant is identified, depending on the initial tissue. During regeneration, cells may be grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Site Specific Integration or Excision of Transgenes

In one embodiment of the invention, techniques for the site-specific integration or excision of transformation constructs may be used in accordance with the invention. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with cells possessing multiple transgene copies, including gene silencing, recombination and unpredictable inheritance, it is typically desirable to control the copy number of the inserted DNA, often only desiring the insertion of a single copy of the DNA sequence.

Site-specific integration or excision of transgenes or parts of transgenes can be achieved in plants by means of homologous recombination (see, for example, U.S. Pat. No. 5,527,695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of approximately $0.5-4.2\times10^{-4}$. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of CaMV (Golic and Lindquist, 1989), the Gin recombinase of phage Mu (Maeser et al., 1991), the Pin recombinase of E. coli (Enomoto et al., 1983), and the R/RS system of the pSR1 plasmid (Araki et al., 1992). The bacteriophage P1 Cre/lox and the CaMV FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently. Experiments on the performance of the FLP/FRT system indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA Segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected DNA can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion.

A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

About: When used with respect to the length of a nucleic acid sequence, means plus or minus ten base pairs.

Expression cassette: A transformation construct from which non-essential portions have been removed prior to introduction into a host genome by genetic transformation. Preferred expression cassettes will comprise all of the genetic elements necessary to direct the expression of a selected gene. Expression cassettes prepared in accordance with the instant invention will include an MtHP promoter.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette therefrom) into a cell in which that exogenous DNA is incorporated into a chromosome or is capable of autonomous replication.

Heterologous coding sequence: Any coding sequence other than the native MtHP coding sequence. A coding sequence is any nucleic acid sequence capable of being transcribed into an mRNA.

Promoter: A recognition site on a DNA sequence or group of DNA sequences that provides an expression control element for a structural gene and to which RNA polymerase specifically binds and initiates RNA synthesis (transcription) of that gene.

Selected DNA: A DNA segment which one desires to introduce into a genome by genetic transformation.

Selected Gene: A gene which one desires to have expressed in a transgenic cell or organism comprising such a cell. A selected gene may be native or foreign to a host genome, but where the selected gene is present in the host genome, will typically include one or more regulatory or functional elements which differ from native copies of the gene.

Transformation construct: A chimeric DNA molecule which is designed for introduction into a host genome by genetic transformation. Preferred transformation constructs will comprise all of the genetic elements necessary to direct the expression of one or more exogenous genes. Transformation constructs prepared in accordance with the instant invention will include a MtHP promoter. The term "transformation construct" specifically includes expression cassettes.

Transgene: A segment of DNA which has been incorporated into a host genome or is capable of autonomous replication in a host cell and is capable of causing the expression of one or more cellular products. Exemplary transgenes will provide the host cell, or organisms comprising such a cell, with a novel phenotype relative to the corresponding non-transformed cell or organism. Transgenes may be directly introduced into a cell genetic transformation, or may be inherited from a cell of any previous generation which was transformed with the DNA segment.

Transgenic cell: A cell or a progeny cell of any generation derived therefrom, wherein the DNA of the cell or progeny thereof contains an introduced exogenous DNA segment not originally present in a non-transgenic cell of the same strain. The transgenic cell may additionally contain sequences which are native to the cell being transformed, but wherein the "exogenous" gene has been altered in order to alter the level or pattern of expression of the gene.

Vector: A DNA molecule capable of replication in a host cell and/or to which another DNA segment can be operatively linked so as to bring about replication of the attached segment.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation of RH2 Sequences from *M. truncatula*

An initial plan was developed to isolate a root-specific promoter by screening a *Medicago truncatula* genomic library using an RH2 cDNA sequence. However, after sequencing the genomic clone, it was found that the exon sequences were different from the RH2 cDNA sequences. The promoter obtained from the genomic clone led to GUS expression not only in roots, but also in other parts of plants. The detailed procedure for isolation of the MtHP promoter is described below.

The expression of pea RH2 gene was reported to be root epidermis-specific (Mylona et al. 1994). This expression profile was initially desired in a new promoter sequence. According to the partial pea RH2 cDNA sequences (Mylona et al. 1994), primers were designed to obtain pea RH2 cDNA sequences by RT-PCR. Sequences of the designed primers were: forward 5' AGAGGCGACTTCCATTGTAGC 3' (SEQ ID NO:4), reverse 5' TAGGAAAGGGAAAAGAAA-GAAAAA 3' (SEQ ID NO:5). Total RNA from pea was used as template in the RT-PCR. The amplified fragment by RT-PCR was used as a probe to screen a cDNA library constructed from phosphate starved roots of *M. truncatula*. Six clones were obtained after screening the cDNA library, and one of the clones, Mt12a, showed highest similarity to pea RH2 sequence. The sequence of Mt12a is given in (FIG. 1) (SEQ ID NO:3). Northern hybridization analyses revealed that Mt12a is only expressed in root tissues of *M. truncatula*, no hybridization signals were detected in leaf, petiole and stem (FIG. 2).

Example 2

Isolation of a Constitutive Promoter (MtHP) from *Medicago truncatula*

Figure 3:
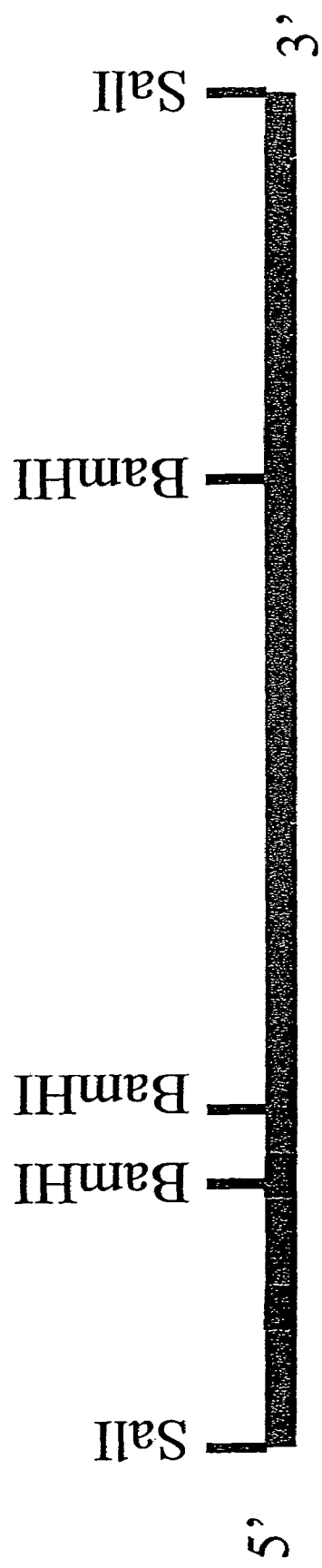
FIG. 3: Schematic restriction map of the genomic clone obtained after screening a *M. truncatula* genomic library using Mt12a as probe.

Mt12a was used to screen a genomic library of *M. truncatula* and a genomic clone was obtained. DNA was isolated from the genomic clone and digested by different restriction enzymes. A schematic restriction map of the genomic clone is shown in FIG. 3. Based on the restriction map (FIG. 3), DNA of the genomic clone was double digested by restriction enzymes Bam HI and Sal I, and the digested fragments were directly subcloned into Bam HI digested- and Bam HI+Sal I digested-pBluescript vector.

Figure 4:
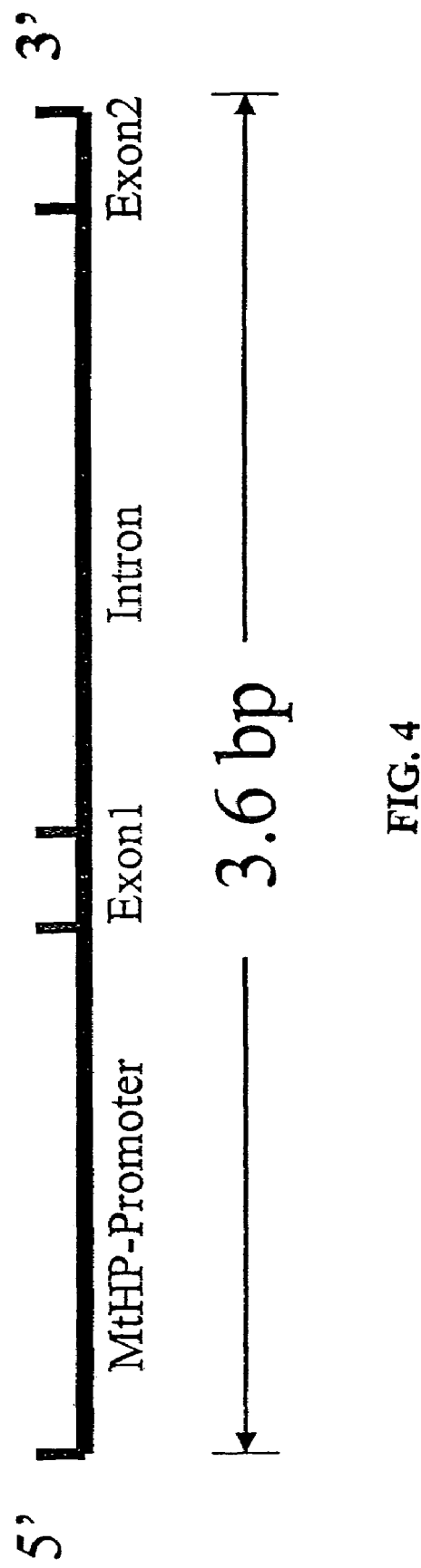
FIG. 4: Structure of the 5' region of the genomic clone obtained after screening a *M. truncatula* genomic library using Mt12a as probe.

Sequencing of subclones revealed the structure of the 5' region of the genomic clone (FIG. 4). The sequence of the 5' region of the genomic clone is shown in FIG. 5, with two exons in lowercase letters. Unexpectedly, the sequences of the exons were different from that of the Mt12a. Since the exon sequences have not been characterized, it was designated MtHP. The sequence was then characterized.

Example 3

In Planta Characterization of the MtHP Promoter

Figure 6:
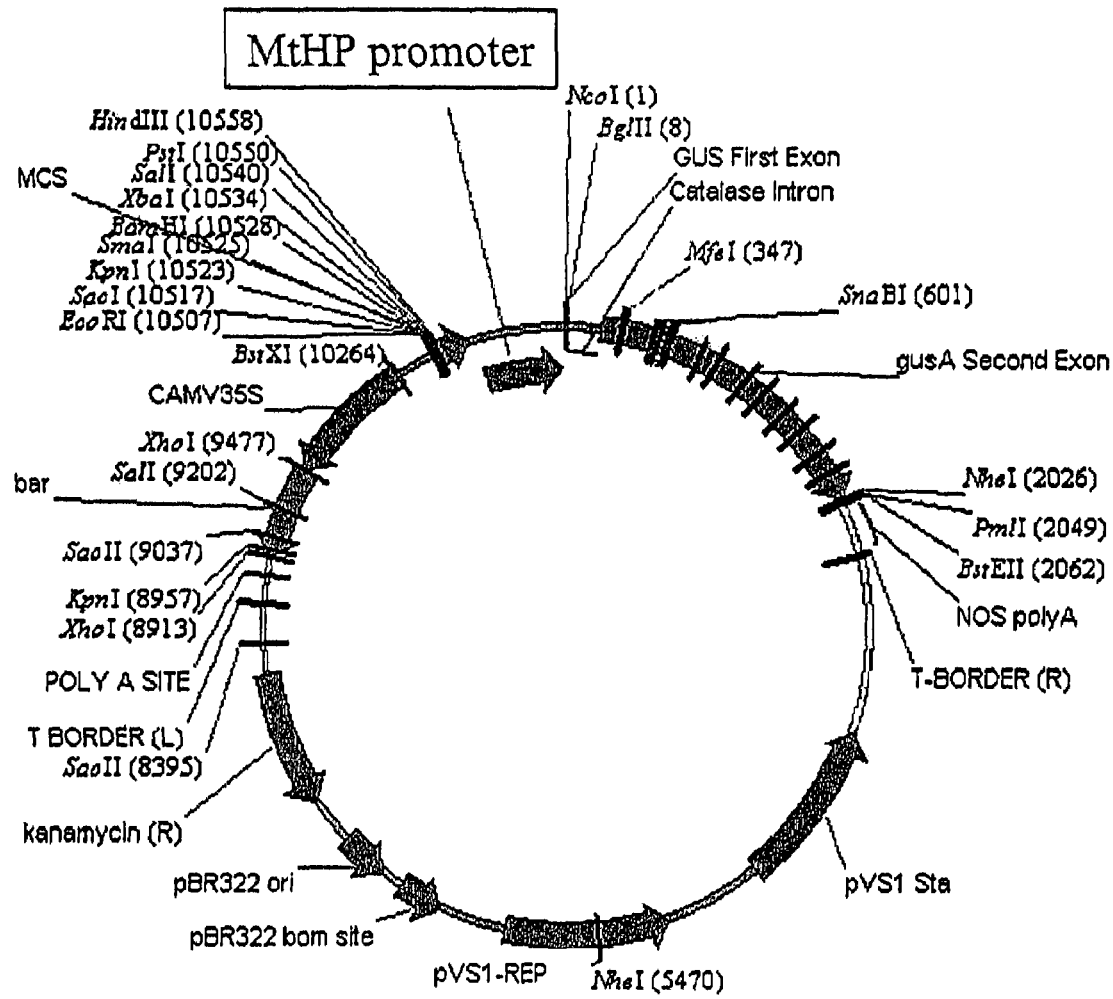
FIG. 6: Map of the MtHP-GUS binary vector used for *Agrobacterium*-mediated transformation

The MtHP promoter region was PCR amplified using primers 5' TTTAAGCTTCTCGATCAATAGTTCAAACC 3' (forward) (SEQ ID NO:6) and 5' GGATCCATGGATG-GTATAATGTATTAAAATGCTA 3' (reverse) (SEQ ID NO:7). The amplified promoter sequences were digested by Hind III and Nco I, and the fragment was isolated. The isolated MtHP promoter fragment was cloned into Hind III and Nco I digested binary vector pCAMBIA3301 to replace the CaMV 35S promoter in front of the gusA gene. The map of the constructed binary vector is shown in FIG. 6. The gusA gene was driven by the MtHP promoter in the vector (FIG. 6). The MtHP-GUS vector was first transferred into *Agrobacterium rhizogenes*, and used for hairy root transformation of *M. truncatula* following the procedure described by Boisson et al. (Boisson et al. 2001).

Figure 8:
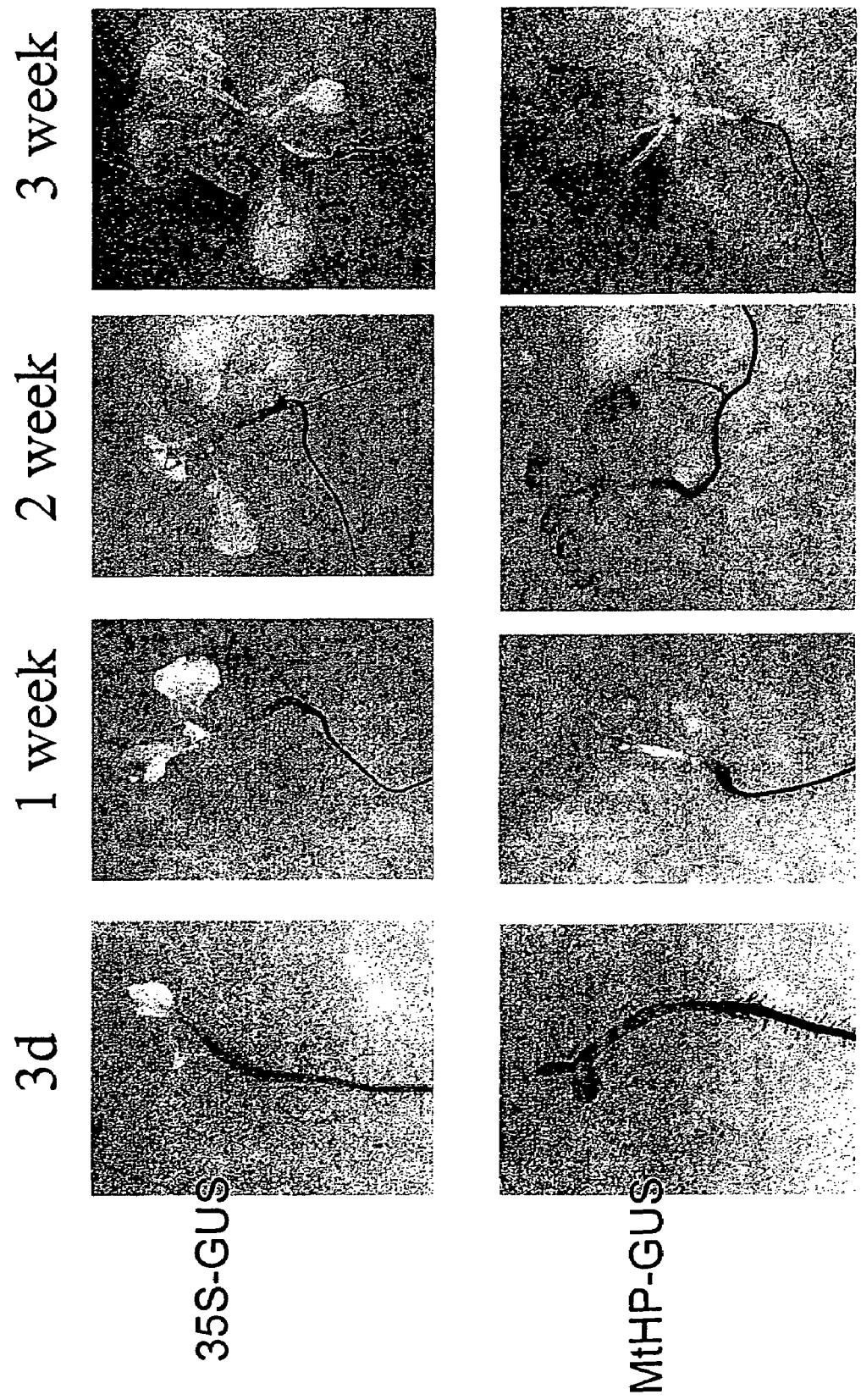
FIG. 8: GUS expression in transgenic *Arabidopsis* plants at different developmental stages.
Figure 10:
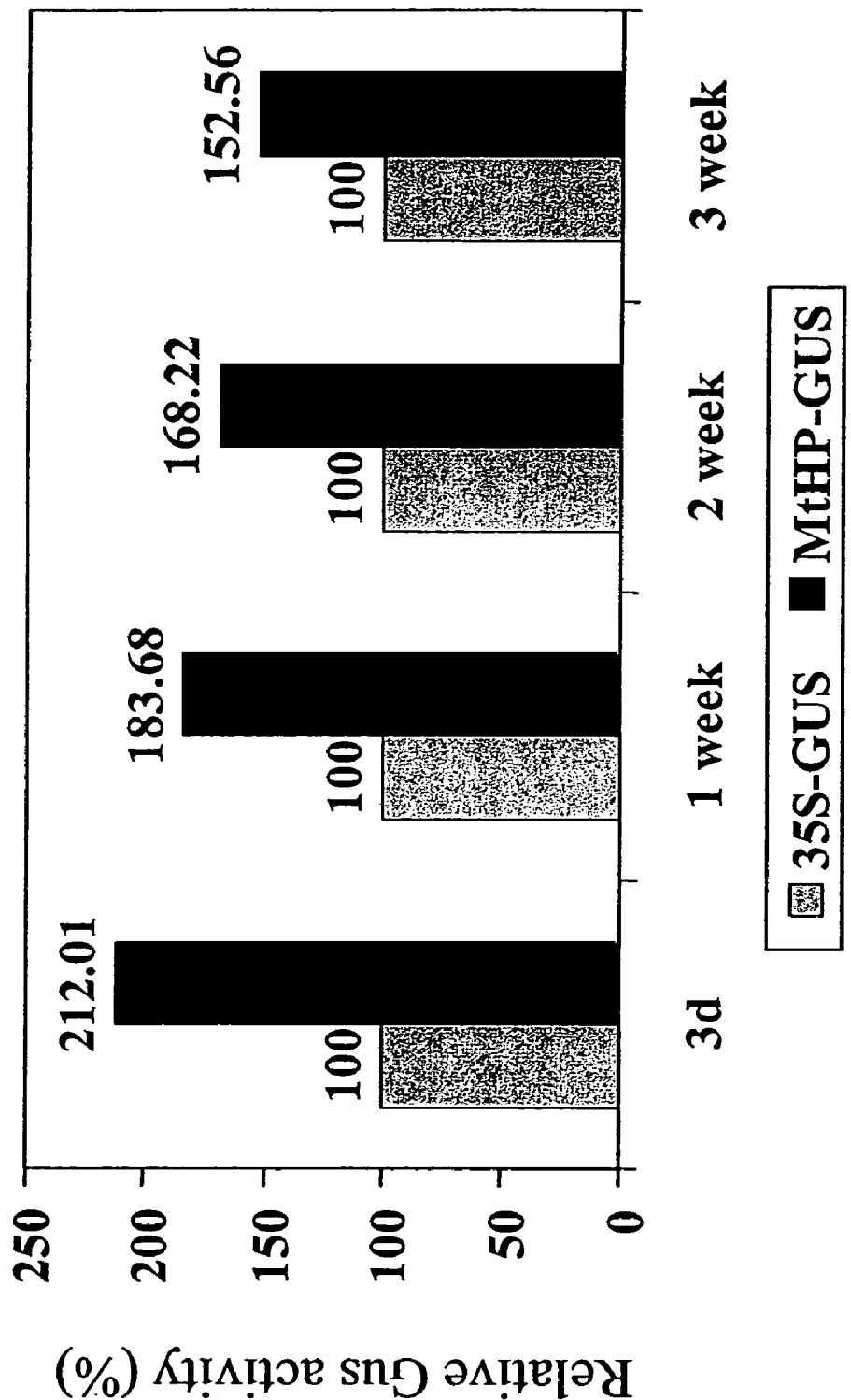
FIG. 10: Relative GUS activity of transgenic *Arabidopsis* plants carrying 35S-GUS and MtHP-GUS gene constructs at different developmental stages.
Figure 11:
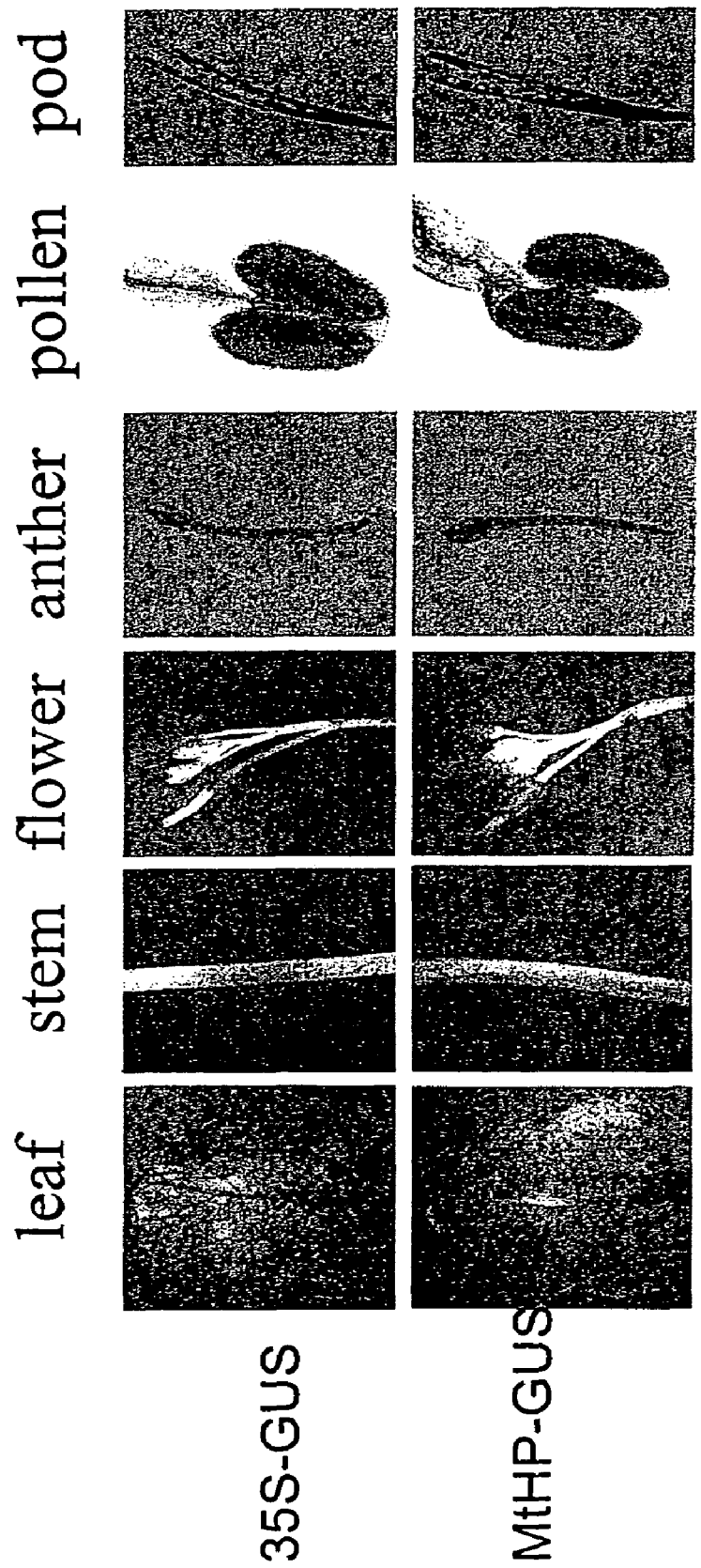
FIG. 11: GUS expression in different tissue and organs of transgenic *Arabidopsis* plants.
Figure 12:
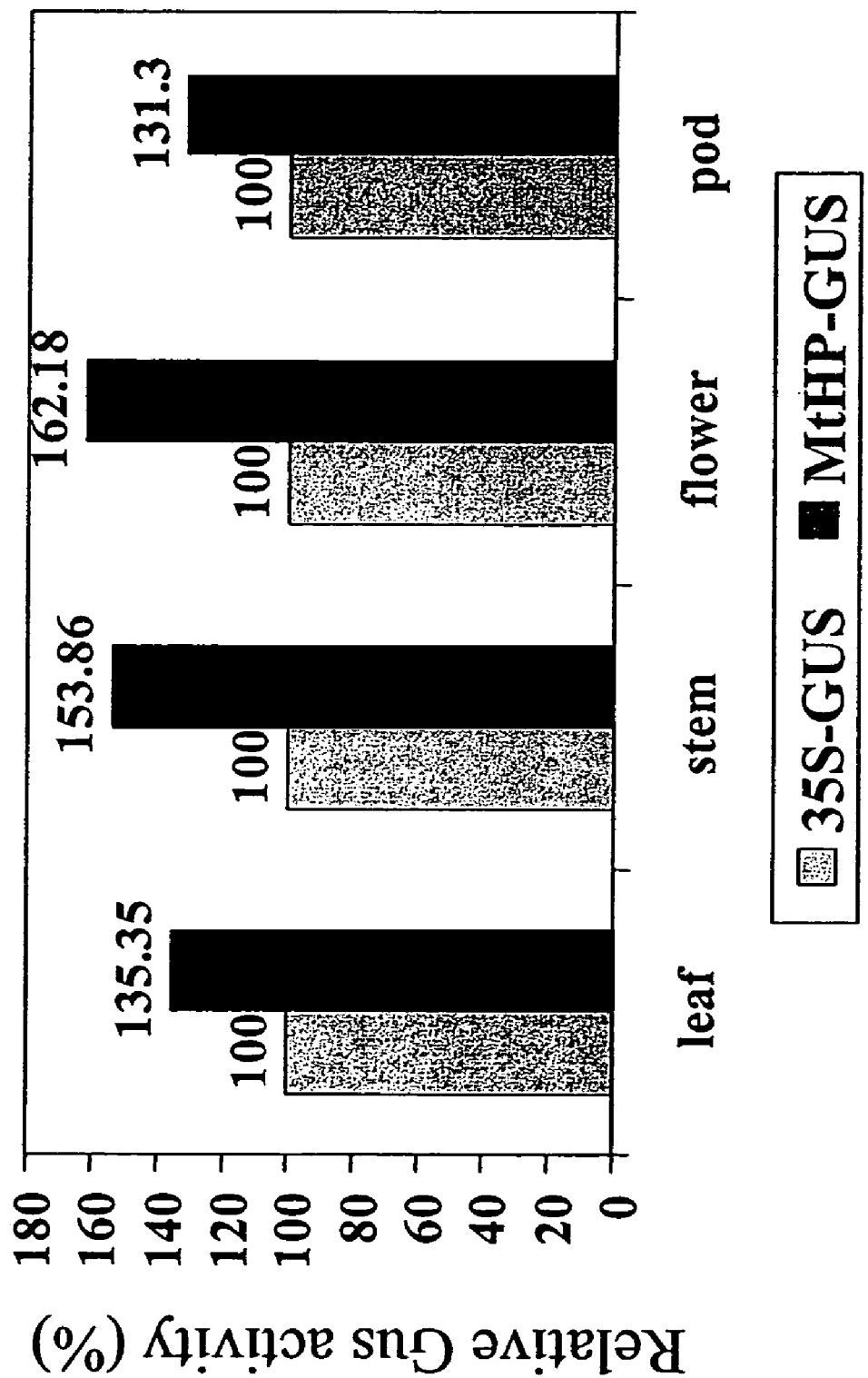
FIG. 12: Relative GUS activity in different tissue and organs of transgenic *Arabidopsis* plants carrying 35S-GUS and MtHP-GUS gene constructs.

The transformed *M. truncatla* hairy root showed blue color after staining with GUS solution (FIG. 7), confirming that the promoter led to gusA expression in root. Because hairy root transformation can only be used to check gene expression in root tissue, the MtHP-GUS vector was transformed into *Agrobocterium tumefaciens* strain C58, and transgenic *Arabidonsis* plants were generated following the floral dip protocol method (dough and Bent 1998). Staining of the transgenic *Arabidopsis* plants revealed strong GUS expression at different developmental stages when MtHP promoter was used to drive the gusA gene (FIG. 8). Although both 35S promoter and MtHP could lead to GUS staining in 3-day, 1-week, 2-week and 3-week old plants levels of GUS expression were consistently higher in MtHP-GUS transgenic plants than that of 35S-GUS plants (FIG. 10). In mature transgenic *Arabidopsis* plants, GUS expression was analyzed in different organs: leaf, stem, flower, anther, pollen and pod (FIG. 11). Again, GUS expression level in different organs was higher in MtHP-OUS tranagenic plants than that in 35S-GUS plants (FIG. 12).

Example 4

Transgenic Expression via the MtHP Promoter in White Clover and Alfalfa

Transgenic white clover plants were obtained following the procedures described by Larkin et al. (1996). Transgenic calluses of alfalfa were obtained following the procedures described by Austin et al. (1995). Strong GUS expression was detected in transgenic white clover plants and transgenic calluses of alfalfa when MtHP promoter was used to drive the gusA gene (FIG. 13).

Example 5

In Planta Transgenic Expression via Deletion Mutants of the MtHP Promoter

Figure 15:
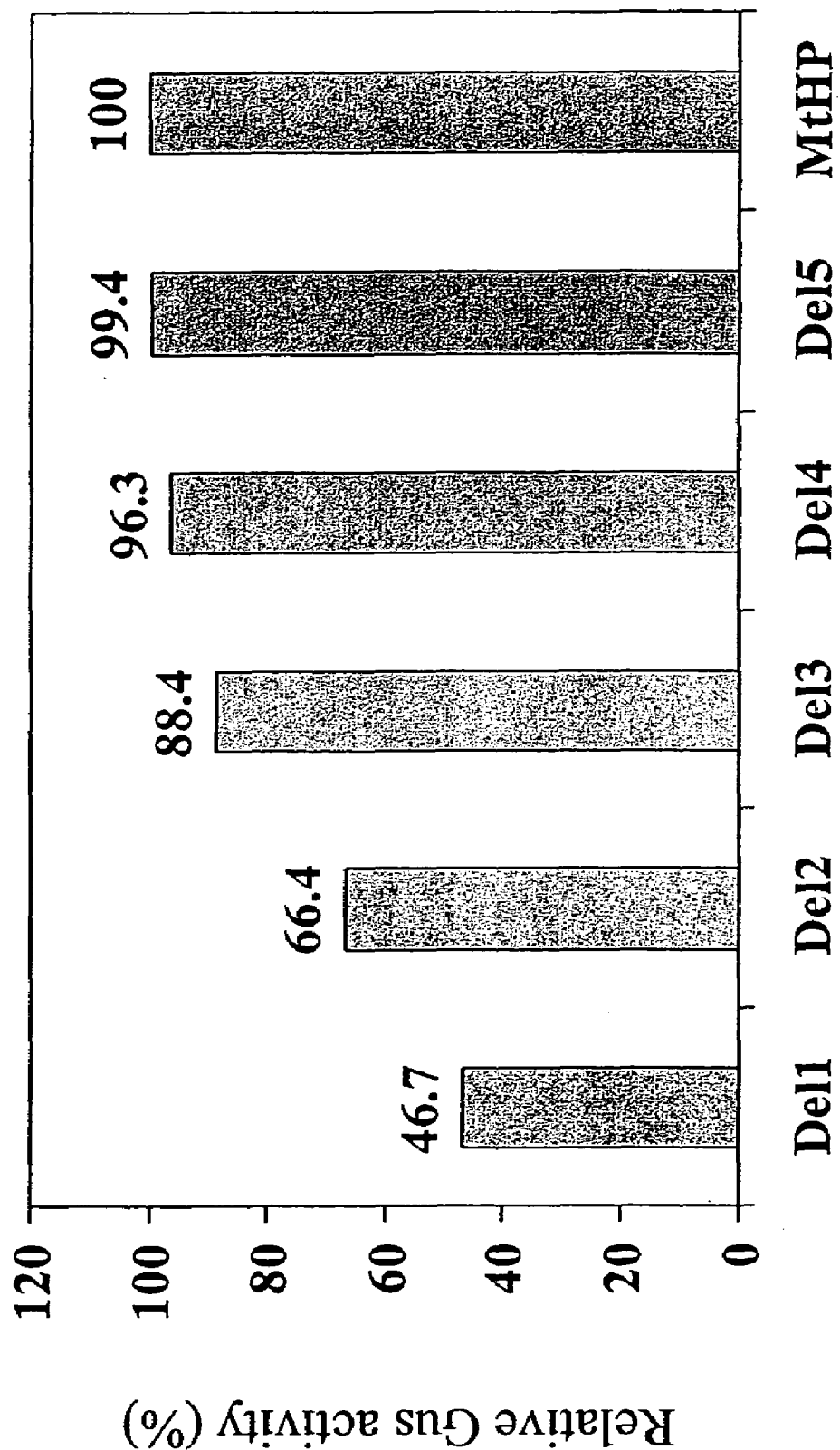
FIG. 15: Relative GUS activity of transgenic *Arabidopsis* plants carrying deleted MtHP-GUS gene constructs with varying lengths of promoter regions.

To further characterize the promoter, a series of deletions of the promoter region were created by PCR using the primers D1 (5' ACTGTACCAAAAAAAGCTTAAATAA 3'; SEQ ID NO:18), D2 (5' AATAGTATATCAAGCTTTTTGT-GAAC 3'; SEQ ID NO:19), D3 (5' ACAAATAGAAGCTT-TATTTAGTCCG 3'; SEQ ID NO:20), D4 (5' CCCATTTT-TAACTAAAGCTTTTTATT 3'; SEQ ID NO:21), D5 (5' AGTAAGCTTCTCCTTTAGATTGAGTC 3'; SEQ ID NO:22) at the 5' end and Rev (5' GGCCATGGATAATG-TATTAAAATGCTAGGT 3'; SEQ ID NO:23) at the 3' end. The use of the D1 (SEQ ID NO:18) and Rev (SEQ ID NO:23) primers resulted in the deletion of 1435 bp from the 5' end of SEQ ID NO:1. The use of the D2 (SEQ ID NO:19) and Rev (SEQ ID NO:23) primers resulted in the deletion of 1290 bp from the 5' end of SEQ ID NO:1. The use of the D3 (SEQ ID NO:20) and Rev (SEQ ID NO:23) primers resulted in the deletion of 1019 bp from the 5' end of SEQ ID NO:1. The use of the D4 (SEQ ID NO:21) and Rev (SEQ ID NO:23) primers resulted in the deletion of 715 bp from 5' end of SEQ ID NO:1. The use of the D5 (SEQ ID NO:22) and Rev (SEQ ID NO:23) primers resulted in the deletion of 424 bp from the 5' end of SEQ ID NO:1. A Hind III restriction site was introduced in the forward primers, and a Nco I restriction site was introduced in the reverse primer. Deletion segments are shown in arrows in FIG. 9. The deleted promoter sequences obtained after PCR amplification were digested by Hind III and Nco I, and were cloned into binary vector pCAMBIA3301 to drive the gusA gene. Gus expression was detected in transgenic *Arabidopsis* plants carrying deleted MtHP-GUS gene constructs with varying lengths of promoter regions (FIG. 14). Even the shortest promoter segment was still able to direct GUS expression in transgenic plants (FIG. 14), although the level of expression was reduced (FIG. 15).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,237,224
U.S. Pat. No. 4,264,731
U.S. Pat. No. 4,273,875
U.S. Pat. No. 4,322,499
U.S. Pat. No. 4,336,336
U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,508,468
U.S. Pat. No. 5,527,695,
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
U.S. Pat. No. 5,641,876
U.S. Pat. No. 5,658,772
Abdullah et al., *Biotechnology*, 4:1087, 1986.
Araki et al., *J. Mol. Biol.* 225(1):25–37, 1992.
Austin et al., *Euphytica*, 85: 381–393, 1995.
Bansal et al., *Proc. Natl. Acad. Sci. USA*, 89:3654–3658, 1992.
Bates, *Mol. Biotechnol.*, 2(2):135–145, 1994.
Battraw and Hall, *Theor. App. Genet.*, 82(2):161–168, 1991.
Bhattacharjee and Gupta, *J. Plant Bioch. and Biotech.* 6:(2):69–73, 1997.
Boisson et al., *Mol. Plant Microbe Interactions*, 14:695–700, 2001.
Bolivar et al., *Gene*, 2: 95–113, 1977.
Bower et al., *Plant Journal*, 2:409–416. 1992.
Buchanan-Wollaston et al., *Plant Cell Reports*, 11:627–631, 1992.
Buising and Benbow, *Mol. Gen. Genet.*, 243(1):71–81, 1994.
Callis et al., *Genes Dev.*, 1:1183–1200, 1987.
Casaetal., *Proc. Natl. Acad. Sci. USA*, 90(23):11212–11216, 1993.
Cashmore et al., *Gen. Eng. of Plants*, Plenum Press, NY, 29–38, 1983.
Chandler et al., *Plant Cell*, 1:1175–1183, 1989.
Christensen, and Quail, *Transgenic Research*, 5(3):213–218, 1996.
Christou et al., *Proc. Natl. Acad. Sci. USA*, 84(12):3962–3966, 1987.
Clough and Bent, *Plant J.*, 16, 735–743, 1998.
Conkling et al., *Plant Physiol.*, 93:1203–1211, 1990.
Cordero et al., *Plant J.*, 6(2)141–150, 1994.
DE 3642 829 A
De Block et al., *EMBO J.*, 6(9):2513–2518, 1987.
De Block et al., *Plant Physiol.*, 91:694–701, 1989.
Dennis et al., *Nucl. Acids Res.*, 12(9):3983–4000, 1984.
D'Halluin et al., *Plant Cell*, 4(12):1495–1505, 1992.
Ebert et al., *Proc. Natl. Acad. Sci. USA*, 84:5745–5749, 1987.
Enomoto, et al., *J. Bacteriol.*, 6(2):663–668, 1983.
European Appl. 154,204
Fraley et al., *Bio/Technology*, 3:629–635, 1985.
Franken et al., *EMBO J.*, 10(9):2605–2612, 1991.
Fromm et al., *Nature* 319:791–793, 1986.
Gelvin et al., In: *Plant Molecular Biology Manual*, 1990.
Ghosh-Biswas et al., *J. Biotechnol.*, 32(1):1–10, 1994.
Golic and Lindquist, *Cell*, 59:3, 499–509, 1989.
Guilley et al., *Cell*, 30:763, 1982.
Hagio et al., *Plant Cell Rep.*, 10(5):260–264, 1991.
Haseloff et al., *Proc. Natl. Acad. Sci. USA*, 94(6):2122–2127, 1997.
He et al., *Plant Cell Reports*, 14 (2–3):192–196, 1994.
Hensgens et al., *Plant Mol. Biol.*, 22(6):1101–1127, 1993.
Hiei et al., *Plant. Mol. Biol.*, 35(1–2):205–218, 1997.
Hou and Lin, *Plant Physiology*, 111: 166, 1996.
Hudspeth and Grula, *Plant Mol. Biol.*, 12:579–589, 1989.
Ishida et al., *Nat. Biotechnol.*, 14(6):745–750, 1996.
Jefferson, *Plant Mol. Biol. Rep.*, 5:387–405, 1987.
Kaeppler et al., *Plant Cell Reports* 9: 415–418, 1990.
Keller et al., *EMBO J.*, 8(5):1309–1314, 1989.
Klee et al., *Bio-Technology*, 3(7):637–642, 1985.
Knittel et al., *Plant Cell Reports*, 14(2–3):81–86, 1994.
Kohler et al., *Plant Mol. Biol.*, 29(6):1293–1298, 1995.
Kunkel et al., *Methods Enzymol.*, 154:367–382, 1987.
Langridge et al., *Proc. Natl. Acad. Sci. USA*, 86:3219–3223, 1989.
Larkin et al., *Transgenic Res.*, 5:325–335, 1996.
Lawton et al., *Plant Mol. Biol.*, 9:315–324, 1987.
Lazzeri, *Methods Mol. Biol.*, 49:95–106, 1995.
Lee et al., *Korean J. Genet.*, 11(2):65–72, 1989.
Lindstrom et al., *Developmental Genetics*, 11: 160, 1990.
Lorz et al., *Mol Gen Genet.*, 199:178–182, 1985.
Maeser et al, *Mol. Gen. Genet.*, 230(1–2):170–176, 1991.
Marcotte et al., *Nature*, 335:454, 1988.
Martinez et al., *J. Mol. Biol.*, 208(4):551–565, 1989.
McCabe and Martinell, *Bio-Technology*, 11(5):596–598, 1993.
McCormac et al., *Euphytica*, 99(1):17–25, 1998.
Murakami et al., *Mol. Gen. Genet.*, 205:42–50, 1986.
Mylona et al., *Plant Mol. Biol.*, 26:39–50, 1994.
Nagatani et al., *Biotech. Tech.*, 11(7):471–473, 1997.
Odell et al., *Nature*, 313:810–812, 1985.
Ogawa et al., *Sci. Rep.*, 13:42–48, 1973.
Omirulleh et al., *Plant Mol. Biol.*, 21(3):415–428, 1993.
Ow et al., *Science*, 234:856–859, 1986.
PCT Appl. WO 9217598
PCT Appl. WO 94/09699
PCT Appl. WO 95/06128
PCT Appl. WO 95/06128
PCT Appl. WO 97/4103
PCT Appl. WO 97/41228
Poszkowski et al., *EMBO J.*, 3:2719, 1989.
Potrykus et al., *Mol. Gen. Genet.*, 199:183–188, 1985.
Poulsen et al., *Mol. Gen. Genet.*, 205(2):193–200, 1986.
Quigley et al., *J. Mol. Evol.*, 29(5):412–421, 1989.
Ralston et al., *Genet.*, 119(1):185–197, 1988.
Reichel et al., *Proc. Natl. Acad. Sci. USA*, 93(12):5888–5893, 1996.
Rhodes et al., *Methods Mol. Biol.*, 55:121–131, 1995.
Ritala et al., *Plant Mol. Biol.*, 24(2):317–325, 1994.
Rochester et al., *EMBO J.*, 5:451–458, 1986.
Rogers et al., *Methods Enzymol.*, 153:253–277, 1987.

Sambrook et al., *In Molecular Cloning: A Laboratory Manual*, Second edition, Cold Spring Harbor Laboratory, Cold Spring Harbor, N.Y., 1989.
Sauer, *Mol. and Cell. Biol.*, 7:2087–2096, 1987.
Schwob et al., *Plant J*, 4(3):423–432, 1993.
Sheen et al., *Plant J.*, 8(5):777–784, 1995.
Simpson, *Science*, 233:34, 1986.
Singsit et al., *Transgenic Res.*, 6(2):169–176, 1997.
Spencer et al., *Plant Molecular Biology*, 18:201–210, 1992.
Stalker et al., *Science*, 242:419–422, 1988.
Sullivan et al., *Mol. Gen. Genet.*, 215(3):431–440, 1989.
Sutcliffe, *Proc. Natl. Acad. Sci. USA*, 75:3737–3741, 1978.
Thillet et al., *J. Biol. Chem.*, 263:12500–12508, 1988.
Thompson et al., *EMBO J.*, 6(9):2519–2523, 1987.
Thompson et al., *Euphytica*, 85(1–3):75–80, 1995.
Tian et al., *Plant Cell Rep.*, 16:267–271, 1997.
Tingayet al., *Plant J.*, 11(6):1369–1376, 1997.
Tomes et al., *Plant. Mol. Biol.* 14(2):261–268, 1990.
Tomic et al., *Nuc. Acids Res.*, 12:1656, 1990.
Torbet et al., *Crop Science*, 38(1):226–231, 1998.
Torbet et al., *Plant Cell Reports*, 14(10):635–640, 1995.
Toriyama et al., *Theor Appl. Genet.*, 73:16, 1986.
Tsukada et al., *Plant Cell Physiol.*, 30(4)599–604, 1989.
Uchimiya et al., *Mol. Gen. Genet.*, 204:204, 1986.
Upender et al., *Biotechniques* 18(1):29–30, 1995.
Van Eck et al., *Plant Cell Reports*, 14(5):299–304, 1995.
Van Tunen et al., *EMBO J.*, 7:1257, 1988.
Vasil et al., *Plant Physiol.*, 91:1575–1579, 1989.
Vodkin et al., *Cell*, 34:1023, 1983.
Vogel et al., *J. Cell. Biochem.*, (Suppl. 0) 13: Part D, 1989.
Walker et al., *Proc. Natl. Acad. Sci. USA*, 84:6624–6628, 1987.
Wang et al., *Mol. Cell. Biol.*, 12(8):3399–3406, 1992.
Watson and Ramstad, *Corn: Chemistry and Technology*, 1987.
Wenzler et al., *Plant Mol. Biol.*, 12:41–50, 1989.
Yamada et al., *Plant Cell Rep.*, 4:85, 1986.
Yang and Russell, *Proc. Natl. Acad. Sci. USA*, 87:4144–4148, 1990.
Zheng and Edwards, *J. Gen. Virol.*, 71:1865–1868, 1990.
Zhou et al., *Plant Cell Reports*, 12(11). 612–616, 1993.

What is claimed is:

1. An isolated nucleic acid sequence comprising a MtHP promoter, the promoter comprising the nucleic acid sequence of SEQ ID NO:1 or a fragment thereof comprising SEQ ID NO:17.

2. The isolated nucleic acid sequence of claim 1, further defined as operably linked to an enhancer.

3. The isolated nucleic acid sequence of claim 1, further defined as operably linked to a coding sequence.

4. The isolated nucleic acid sequence of claim 1, further defined as comprising the nucleic acid sequence of SEQ ID NO:13, SEQ ID NO:14, SEQ ID NO:15, or SEQ ID NO:16.

5. A transformation construct comprising:
(a) an isolated nucleic acid sequence comprising a MtHP promoter, the promoter comprising the nucleic acid sequence of SEQ ID NO:1 or a fragment thereof comprising SEQ ID NO:17; and
(b) a heterologous coding sequence operably linked to said MtHP promoter.

6. The transformation construct of claim 5, wherein the coding sequence is operably linked to a terminator.

7. The transformation construct of claim 5, further comprising an enhancer.

8. The transformation construct of claim 5, further comprising a selectable marker.

9. The transformation construct of claim 5, further comprising at least a second promoter.

10. The transformation construct of claim 9, further comprising at least a second heterologous coding sequence operably linked to said second promoter.

11. The transformation construct of claim 5, further comprising a screenable marker.

12. The transformation construct of claim 5, wherein the isolated nucleic acid sequence comprises the nucleic acid sequence of SEQ ID NO:13, SEQ ID NO:14, SEQ ID NO:15, or SEQ ID NO:16.

13. A plant transformed with a selected DNA comprising a MtHP promoter operably linked to a heterologous coding sequence, wherein said promoter comprises the nucleic acid sequence of SEQ ID NO:1 or a fragment thereof comprising SEQ ID NO:17.

14. The plant of claim 13, further defined as a dicotyledonous plant.

15. The plant of claim 14, wherein the dicotyledonous plant is tobacco, alfalfa, tomato, potato, clover, soybean, cotton, canola, or sunflower.

16. The plant of claim 13, further defined as a monocotyledonous plant.

17. The plant of claim 16, wherein the monocotyledonous plant is wheat, maize, rye, rice, oat, barley, turfgrass, sorghum, millet or sugarcane.

18. The plant of claim 13, wherein the promoter comprises the nucleic acid sequence of SEQ ID NO:13, SEQ ID NO:14, SEQ ID NO:15, or SEQ ID NO:16.

19. A cell of the plant of claim 13, wherein said cell comprises said selected DNA.

20. A seed of the plant of claim 13, wherein said seed comprises said selected DNA.

21. A progeny plant of any generation of the plant of claim 13, wherein said progeny plant comprises said selected DNA.

22. A method of expressing a polypeptide in a plant cell comprising the steps of:
(a) obtaining a construct comprising a MtHP promoter operably linked to a heterologous coding sequence, wherein said promoter comprises the nucleic acid sequence of SEQ ID NO:1 or a fragment thereof comprising SEQ ID NO:17; and
(b) transforming a recipient plant cell with the construct, wherein said recipient plant cell expresses said selected polypeptide.

23. The method of claim 22, wherein the plant cell is further defined as a dicotyledonous plant cell.

24. The method of claim 23, wherein the dicotyledonous plant cell is from tobacco, tomato, potato, clover, soybean, canola, alfalfa, sunflower or cotton.

25. The method of claim 22, wherein the plant cell is further defined as a monocotyledonous plant cell.

26. The method of claim 25, wherein the monocotyledonous plant cell is from wheat, maize, rye, rice, oat, barley, turfgrass, sorghum, millet or sugarcane.

27. The method of claim 22, wherein the promoter comprises the nucleic acid sequence of SEQ ID NO:13, SEQ ID NO:14, SEQ ID NO:15, or SEQ ID NO:16.

28. A method of producing a plant transformed with a selected DNA comprising a MtHP promoter operably linked to a heterologous coding sequence, wherein said promoter comprises the nucleic acid sequence of SEQ ID NO:1 or a fragment thereof comprising SEQ ID NO:17, comprising:
(a) obtaining a first plant comprising said selected DNA;
(b) crossing said first plant to a second plant lacking said selected DNA; and (c) obtaining at least a first progeny plant resulting from said crossing, wherein said progeny plant has inherited said selected DNA.

29. The method of claim 28, wherein the plant is further defined as a dicotyledonous plant.

30. The method of claim 29, wherein the dicotyledonous plant is tobacco, clover, tomato, potato, soybean, canola, alfalfa, sunflower or cotton.

31. The method of claim 28, wherein the progeny plant is a monocotyledonous plant.

32. The method of claim 31, wherein the plant is wheat, maize, rye, rice, oat., barley, turfgrass, sorghum, millet or sugarcane.

33. The method of claim 28, wherein the promoter comprises the nucleic acid sequence of SEQ ID NO:13, SEQ ID NO:14, SEQ ID NO:15, or SEQ ID NO:16.

* * * * *